(12) United States Patent
Baltz et al.

(10) Patent No.: US 7,791,028 B2
(45) Date of Patent: Sep. 7, 2010

(54) APPARATUS AND METHOD FOR SYSTEM IDENTIFICATION

(75) Inventors: Nathan T. Baltz, Boulder, CO (US); J. D. Sheldon Danielson, Boulder, CO (US)

(73) Assignee: TauTheta Instruments LLC, Boulder, CO (US)

( * ) Notice: Subject to any disclaimer, the term of this patent is extended or adjusted under 35 U.S.C. 154(b) by 532 days.

(21) Appl. No.: 11/598,349

(22) Filed: Nov. 13, 2006

(65) Prior Publication Data

US 2007/0114443 A1    May 24, 2007

Related U.S. Application Data

(60) Provisional application No. 60/736,021, filed on Nov. 10, 2005.

(51) Int. Cl.
*G01F 23/00* (2006.01)
*G01T 1/20* (2006.01)

(52) U.S. Cl. .................... 250/358.1; 250/362

(58) Field of Classification Search ........... None
See application file for complete search history.

(56) References Cited

U.S. PATENT DOCUMENTS

| | | | |
|---|---|---|---|
| 4,716,363 A | 12/1987 | Dukes et al. | |
| 5,030,420 A | 7/1991 | Bacon et al. | |
| 5,119,322 A | 6/1992 | Stroobach | |
| 5,270,548 A | 12/1993 | Steinkamp | |
| 5,462,879 A | 10/1995 | Bentsen | |
| 5,757,013 A | 5/1998 | Groger et al. | |
| 6,157,037 A | 12/2000 | Danielson | |
| 6,325,978 B1 | 12/2001 | Labuda et al. | |
| 6,479,822 B1 * | 11/2002 | Nelson et al. | 250/341.1 |
| 6,563,585 B1 | 5/2003 | Rao et al. | |
| 6,597,000 B2 * | 7/2003 | Stern | 506/12 |
| 6,664,111 B2 | 12/2003 | Bentsen et al. | |
| 6,771,767 B1 * | 8/2004 | Li et al. | 379/386 |
| 6,815,211 B1 | 11/2004 | Blazewicz et al. | |
| 6,912,050 B2 | 6/2005 | Inberg | |
| 6,950,511 B2 | 9/2005 | Das et al. | |
| 2006/0022145 A1 * | 2/2006 | McLoskey et al. | 250/458.1 |
| 2007/0036211 A1 * | 2/2007 | Kajiwara | 375/232 |

FOREIGN PATENT DOCUMENTS

| | | |
|---|---|---|
| EP | 0612997 A2 | 8/1994 |
| WO | 9731246 A | 8/1997 |

(Continued)

OTHER PUBLICATIONS

Sanchez, International Search Report and Written Opinion in related PCT application Serial No. PCT/US2006/043868, Mar. 23, 2007.

(Continued)

*Primary Examiner*—David P Porta
*Assistant Examiner*—Carolyn Igyarto
(74) *Attorney, Agent, or Firm*—Lathrop & Gage LLP

(57) ABSTRACT

Methods and apparatus for system identification operate by computing phase and amplitude using linear filters. By digitally processing the linearly filtered signals or data, the phase and amplitude based on measurements of the input and output of a system, are determined.

16 Claims, 11 Drawing Sheets

FOREIGN PATENT DOCUMENTS

WO  WO/2005/099092  *  3/2005

OTHER PUBLICATIONS

Ozdemir, A., et al., "Low Cost Missed-Signal Microcontroller Based Power Measurement Technique" IEE Proceedings-Science, Measurement & Technology, vol. 151, No. 4, pp. 253-258, Jul. 2, 2004.

Lyons, R., et al., "The Swiss Army Knife of Digital Networks," IEEE Signal Processing Magazine, vol. 21, No. 3, pp. 90-100, May 2004.

Simetkosky, T., et al., "A Modified Goertzel Structure for Efficient Real-Time BloodVelocity profile Estimation," 2002 IEEE International Conference on Acoustics, Speech, and Signal Processing, Proceedings, (CAT. No. 02CH37334), vol. 4, pp. IV3884-IV3887, 2002.

Beck, R., et al., "Finite-Precision Goertzel Filters Used For Signal Tone Detection," IEEE Transactions On circuits And Systems II: Analog And Digital Signal Processing, vol. 48, No. 7, pp. 691-700, Jul. 2001.

Morgan, D., "More Tools For Spectral Analysis," Embedded System Program, vol. 12, No. 6, pp. 87-91, Jun. 1999.

Brown, A., "Goertzel Alternative To the Fourier Transform," Electronics World + Wireless World, vol. 99, pp. 485-487, Jun. 1993.

Marganitz, A. "Anwendung des Goertzel-Agorithmus Zur Detektion von Sinussignalen, Application of Goertzel Algorithm For The Detection of Sinusoidal Signals," vol. 44, No. 9-10, pp. 258-261, Sep.-Oct. 1990, Only Abstract translated; Only Abstract and Figs. considered.

Piety, K.R., et al., "Development And Implementation of an On-Line Fourier Analyzer Based on the Goertzel Method," Transactions of the American Nuclear Society, vol. 18, pp. 139-140, Jun. 1974.

Alacla, J., et al., "Digital Phosphorimeter With Frequency Domain Signal Processing: Application To Real-Time Fiber-Optic Oxygen Sensing," Review of Scientific Instruments, vol. 64, No. 6, pp. 1554-1560, Jun. 1993.

Liao, S., et al., "Real-Time Frequency Domain Temperature And Oxygen Sensor With a Single Optical Fiber," IEEE Transactions on Biomedical Engineering, vol. 44, No. 11, pp. 1114-1121, Nov. 1997.

Stehning, C., et al., "Addressing Multiple Indicators on a Single Optical Fiber—Digital Signal Processing Approaches For Temperature Compensated Oxygen Sensing," IEEE Sensors Journal, vol. 4, No. 1, pp. 153-159, Feb. 2004.

Banks, K., The Goertzel Algorithm, Embedded System Design, Aug. 28, 2002, http://www.embedded.com/shared/printableArticle.jhtml?articleID=9900722, retrieved Sep. 15, 2006.

Jagudits, L., "Dual Tone Detection by Goertzel Algorithm" Acta Polytechnica Ceske Vysoke Uc Tech. Prace III,, No. 12(III3), pp. 63-68, 1989.

Banks, K., The Goertzel Algorithm, Embedded System Program, vol. 15, No. 9, pp. 34-42, Sep. 2002.

Neumeuer, D., et al., "Application of Goertzel Algorithm For Unbalance Signal Processing," IMechE Event Publication; vol. 2004 2, pp. 291-299; 2004.

Krohn-Hite Model 3940, Krohn-Hite Corporation, Copyright © Apr. 21, 2006, downloaded from the Internet Oct. 15, 2009, http://www.krohn-hite.com/htm/filters/mod3940.htm, 2 pages.

Krohn-Hite Corporation, Obsolete and Replacement Models, Copyright @ Feb. 19, 2006 downloaded from the Internet Oct. 15, 2009. http://www.krohn-hite.com/htm/ReplaceModel.htm, 1 page.

Frequency Devices, 824 Series: Programmable Electronic Filters, 2007 retrieved from the Internet Oct. 13, 2009, http://www.frequencydevices.com/products/filters/824.html, 9 pages.

European Application No. 06 837 371.1, Office Communication dated Feb. 11, 2009, 3 pages.

European Application No. 06 837 371.1, Response to Office Communication, Aug. 19, 2009, 11 pages.

Australian Patent Application No. 2006315664, Examiner's Report dated May 26, 2010, 2 pages.

* cited by examiner

APPARATUS AND METHOD FOR SYSTEM IDENTIFICATION

RELATED APPLICATIONS

This application claims priority and is related to U.S. Provisional Patent Application, Ser. No. 60/736,021, entitled: Method of Phase Delay Measurement with a Linear IIR Digital Filter, filed Nov. 10, 2005, the entire disclosure of which is incorporated by reference herein.

GOVERNMENT SUPPORT

The disclosed subject matter was made with Government Support under a Phase II SBIR Contract with DOD-Air Force #FA8650-05-C-5001.

TECHNICAL FIELD

The disclosed subject matter is in the field of system identification. In particular, the disclosed subject matter is directed to luminescence systems and methods for measuring phase shifts between excitation light or excitation energy and emission light or emission energy for system identification.

BACKGROUND

Luminescent sensors have seen tremendous growth in applications for measurement of chemical analytes such as oxygen, carbon dioxide and pH. Many of these luminescent sensors are well approximated by a single or multi-exponential model. This is particularly useful, because with one or two excitation (stimulus) frequencies, the time constant(s) of the system (luminescence lifetime decay) can be estimated.

For example, oxygen concentrations in samples such as water, are typically measured with devices that employ a luminescent probe molecule embedded in a sensing matrix. These devices measure light emitted from the luminescent probe molecule. The luminescent light is generated after excitation light has been directed to the sensing matrix containing the luminescent probe. There is a phase shift between the excitation light and the luminescent light that is measured by the device, that changes with oxygen concentration. The phase shift is then used in an empirically derived calibration, or theoretical model that relates phase shift of the luminescent probe to oxygen concentration in the sensing matrix.

Alternately, the luminescent lifetime may be calculated from the measured phase shift, and the oxygen concentration in the sensing matrix is related to the lifetime using an empirically derived or theoretical model. The oxygen concentration within the sensing matrix is generally proportional to the oxygen concentration of the sample (water), and is typically related by Henry's law. Other analytes, for example, $CO_2$, pH, glucose, in samples are evaluated similarly, as the sensing matrix and luminescent probe are tailored for sensitivity to these particular analytes. The luminescent lifetime may be calculated from the measured phase shift, and the analyte concentration in the sensing matrix is related to the lifetime using an empirically derived or theoretical model.

Contemporary apparatus, that perform the above described functions, operate by measuring phase shift of the luminescent probe. These apparatus include a digital signal processor in communication with a synthesizer that generates a sinusoidally modulated electrical signal, and light emitting diodes (LEDs) driven by the sinusoidally modulated electrical signal. There is normally an optical filter, that improves the spectral purity of the LED, a sensing matrix that contains the luminescent probe, an emission filter that only passes the emission of the luminescent probe, and, a photodiode or similar device for converting the emitted luminescence, from the luminescent probe, into an electrical signal. These apparatus also have analog to digital converters that convert the electrical signal into a digital representation.

When the LEDs direct excitation light to the luminescent probe, the photodiode detects the emitted luminescence, and an analog to digital converter converts the emitted luminescence into a digital signal. The systems then determine the phase shift, between the sinusoidally modulated excitation light and the emitted luminescence. The digital signal processor that generates the sinusoidally modulated excitation signal can also be used to compute the phase difference between the excitation signal and the emitted luminescence. Based on the phase shift, the requisite measurement, quantity, or the like, may be determined.

U.S. Pat. No. 4,716,363 to Dukes, discloses an exemplary contemporary apparatus, that measures luminescence lifetime. The luminescence lifetime is determined by a comparison, performed by an analog processing system that implements a phase-locked servo loop. This servo loop varies the frequency of the modulated excitation light to maintain a constant phase shift between the excitation and emission of the luminescent probe. The analyte concentration is related to the resultant frequency, or the lifetime is calculated from the resultant frequency and phase. The analyte concentration is related to the calculated lifetime.

This apparatus exhibits drawbacks, in that the servo loop takes a long time to settle and it is not suited to measurements where the excitation light is turned on for short durations. Short duration measurements are desirable because the consumption of electric power is reduced and photodegradation of the sensing matrix is minimized. Moreover, the components of the apparatus must operate over a wide range of frequencies, which means that they are expensive and consume large amounts of power.

Another exemplary contemporary apparatus is disclosed in U.S. Pat. No. 6,157,037 to Danielson. This apparatus uses phase comparison, as a digital signal processor, that generates sinusoidally modulated excitation light, and implements a servo loop that varies both the modulation frequency and the phase shift through the luminescent sample. The analyte concentration is related to the resultant phase or frequency, or, calculated lifetime.

This apparatus exhibits drawbacks, in that, like the apparatus of U.S. Pat. No. 4,716,363, the servo loop takes a long time to settle. This long settling time increases the amount of time that the luminescent probe is exposed to excitation light, which can cause the luminescent probe to degrade. Additionally, the implementation of the servo loop in a digital signal processor would be computationally intensive, and requires a device with a high CPU clock frequency, and typically a hardware multiplier. Moreover, the use of sinusoidally modulated excitation is computationally intensive and requires multiple additional apparatus components, in addition to a digital processor. Also, the components necessary to perform these functions are expensive, and consume large amounts of power.

Another exemplary contemporary apparatus is disclosed on U.S. Pat. No. 6,664,111 to Bentsen. One disclosed apparatus uses sinusoidally, amplitude modulated light from an oscillator, or from a Direct Digital Synthesis (DDS) device, to excite an oxygen sensitive luminescent probe. The implementation uses a Discrete-Time Fourier Transform algorithm. The apparatus then acquires data representing the emitted luminescence, and subsequently applies a Discrete-Time Fourier Transform or Fast Fourier Transform (FFT) vector analysis method on the data to calculate the phase shift of the luminescent probe. Alternately, the phase shift is calculated by a least squares algorithm on the data. Both the Discrete-Time Fourier Transform method and least squares algorithm were implemented on software running on a personal computer.

This apparatus exhibits drawbacks in that both algorithms are sensitive to frequency errors and offsets. These frequency errors can cause errors in the measured phase and amplitude. Depending on the Fourier implementation, such as the Fast Fourier Transform, this method could also have large memory requirements. Additionally, the use of sinusoidally modulated excitation is computationally intensive and requires multiple additional system components, in addition to a digital processor. Also, the Discrete-Time Fourier Transform and least squares algorithm are computationally intensive, requiring complex and expensive components, large amounts of memory, and these components and memory consume large amounts of power.

SUMMARY

The disclosed subject matter, including apparatus (systems and/or devices) and methods for use thereof, improve on the contemporary art, as the disclosed subject matter allows for the measurement of phase shift of a luminescent probe using small, low power, low cost digital processors, or microcontrollers, without the need for synthesizing a sinusoidally modulated excitation light. Additionally, the disclosed subject matter is computationally simplified, uses simple off the shelf components, that when combined do not consume large amounts of power. Moreover, these components are such that they eliminate the need for multiplication in real-time, and eliminate requirements of buffering large amounts of data in memory before processing. Also, the disclosed subject matter provides short measurement times, that reduce power consumption of the apparatus and photodegredation of the luminescent probes.

The disclosed subject matter includes methods and apparatus for system identification, that compute phase and amplitude using linear filters. By digitally processing the linearly filtered signals or data, the phase and amplitude based on measurements of the input and output of a system, are determined.

The disclosed apparatus and methods provide second order linear filters for use in efficiently calculating phase and/or amplitude of signals, output by a system, for example, a physical or linear system. The system may include an electrical network, an electromechanical oscillator, or a luminescent material. The systems have inputs and outputs, and may be characterized by providing an input of known phase and amplitude at a known frequency, and measuring the output phase and amplitude of the physical system. The phase and amplitude of the output can be used to calculate quantities, such as amounts of dissolved oxygen.

The disclosed subject matter works with numerous systems for system identification. These systems may be for example, electrical systems, typically a Resistance/Capacitance (RC) network, where the capacitance varies with some unknown parameter. The system may also be an electromechanical system such as a quartz-crystal oscillator, where its resonant frequency and Q are the unknown parameters. The system may also be an electro-chemical system with electrodes, where a chemical reaction is taking place with unknown kinetics. The system may also be a medium that absorbs light that is dependant on some unknown parameter. Yet another system may be a luminescent sensor, where light is absorbed and emitted with some time constant which depends on an unknown parameter.

In some applications, both phase and amplitude information are valuable measurements that can be used to find the unknown parameter. In other applications phase or amplitude are important measurements, but not both. The determination is partly dependent on the nature of the system and is left up to the designer. In Impedance Spectroscopy, for example, typically a range of frequencies are used to stimulate the system, either sequentially or in parallel, to gather information related to both the amplitude and phase response of the system. In other applications such as luminescence, the phase measurement is sufficient, and typically more reliable than an intensity measurement, to find the unknown parameter. This preference for phase over amplitude in luminescence systems is due to a number of factors some of which are variable optical collection efficiency, fiber optic size, fiber bending and optical scattering from the sensor, all of which can cause changes in measured amplitude but usually not in the measured phase.

The disclosed subject matter avoids the disadvantages of techniques with high computational complexity and requirements for storing and processing large data sets. Rather, the disclosed systems and methods require only a small number of calculations to be performed, as each sample is received in the digital processor. The calculations are preferably limited to additions and subtractions, with intermediate results stored in a small allotment of memory. Additionally, the real-time data processing requirements are minimal so that an inexpensive microcontroller or digital processor can be used.

The disclosed subject matter includes components that perform second order filter algorithms. These second order filter algorithms include a modified Goertzel Algorithm. The modified Goertzel Algorithm is typically performed at least partially by a second order filter, that is typically a linear filter, by, for example, an infinite impulse response (IIR) filter, that is included in the second order filter component. By performing the modified Goertzel Algorithm, the disclosed subject matter, does not need to employ computationally intensive and time consuming Discrete Fourier Transform (DFT) or Fast Fourier Transforms (FFT) methods, when calculating phase and/or amplitude in system identification problems. Moreover, memory usage of the disclosed second order filter algorithm is quite minimal. The maximum number of stored coefficients is three and the maximum memory needed for the filter is also three.

The disclosed subject matter is directed to a method for system identification. The method includes, exciting a system by directing a first waveform to the system, detecting a second waveform emitted from the system, and analyzing at least one signal corresponding to the detected waveform emitted from the system by linearly filtering the at least one signal. The system may be for example, a luminescent probe, and the analysis may be for phase shift, amplitude or other desired measurement or quantity. For example, by determining the phase shift of a luminescent system, a concentration of oxygen in water can be determined.

The disclosed subject matter is also directed to a method for analyzing light emissions from a luminescent sample, that defines a system. The method includes, providing excitation light to the luminescent sample and detecting emitted luminescence from the luminescent sample. The emitted luminescence is analyzed by linearly filtering the output corresponding to the detected emitted luminescence. The linear filtering is typically performed by components including a linear filter, such as a second order digital linear filter. This second order digital linear filter, may be, for example, an infinite impulse response (IIR) filter.

Also disclosed is an apparatus for system identification. The apparatus includes a source of a first waveform for exciting a system, a detector for detecting a second waveform emitted from the system, and a converter for converting the second waveform into output signals corresponding to the second waveform. There is also a linear filter component for analyzing the output signals corresponding to the second waveform.

There is also disclosed a luminescent light measurement apparatus. The apparatus includes an excitation light source, for example, a light emitting diode (LED), for transferring excitation light to a luminescent probe. The luminescent probe is such that it transfers emission light in response to the excitation light. There is a detector system for detecting the emission light, and generating at least one signal corresponding to the emission light. The detector typically includes a photodiode. The apparatus also includes, a linear filter component for processing the at least one signal, and, a processor, electrically coupled to the linear filter component for determining the phase shift between the excitation light, from the excitation light source, and the emission light, emitted by the luminescent probe. The linear filter component typically includes a linear filter, electrically coupled with control logic, such as processors and the like. The linear filter component performs its filtering function by employing a modified Goertzel algorithm. The linear filter, may be, for example, a second order digital linear filter, such as an infinite impulse response (IIR) filter.

The disclosed subject matter is also directed to a down-converting apparatus for stem identification. The down converting apparatus includes, a source of a periodic waveform for exciting a system, a detector for detecting a second periodic waveform in response to the first periodic waveform exciting the system, and a generator for generating a third periodic waveform. There is also a mixing unit for mixing at least two of the first periodic waveform, the second periodic waveform and the third periodic waveform to generate down converted fourth and fifth periodic waveforms. The mixing unit typically includes two mixers, for example, analog mixers. There is also at least one linear filter component for analyzing signals corresponding to each of the down converted fourth and fifth periodic waveforms. The periodic waveforms may be, for example, sine waves or square waves.

The disclosed subject matter is also directed to a method for analyzing down-converting waveforms for system identification the method includes exciting a system by transferring a first periodic waveform to the system, detecting a second periodic waveform in response to the first periodic waveform exciting the system and generating a third periodic waveform. At least two of the first periodic waveform, the second periodic waveform and the third periodic waveform are mixed to generate down converted fourth and fifth periodic waveforms; and, at least one signal corresponding to each of the down converted fourth and fifth periodic waveforms is analyzed by linearly filtering signals corresponding to each of the down converted fourth and fifth periodic waveforms.

BRIEF DESCRIPTION OF THE DRAWINGS

Attention is now directed to the drawing figures, where like or corresponding numerals indicate like or corresponding components. In the drawings.

DETAILED DESCRIPTION

The subject matter disclosed herein is directed to apparatus and methods that utilize linear filters, such as second order linear filters, in apparatus for system identification. The linear filters are portions of components, that utilize modified Goertzel Algorithms to determine, for example, the phase shift in a luminescent sample or other system, typically a linear or physical system. The disclosed subject matter, with its use of linear filters, is highly efficient in computing phase or amplitude based on measurements of excitation light and emitted light from a luminescent sample or phase and amplitude of input and output electrical signals of an impedance network.

Figure 1:
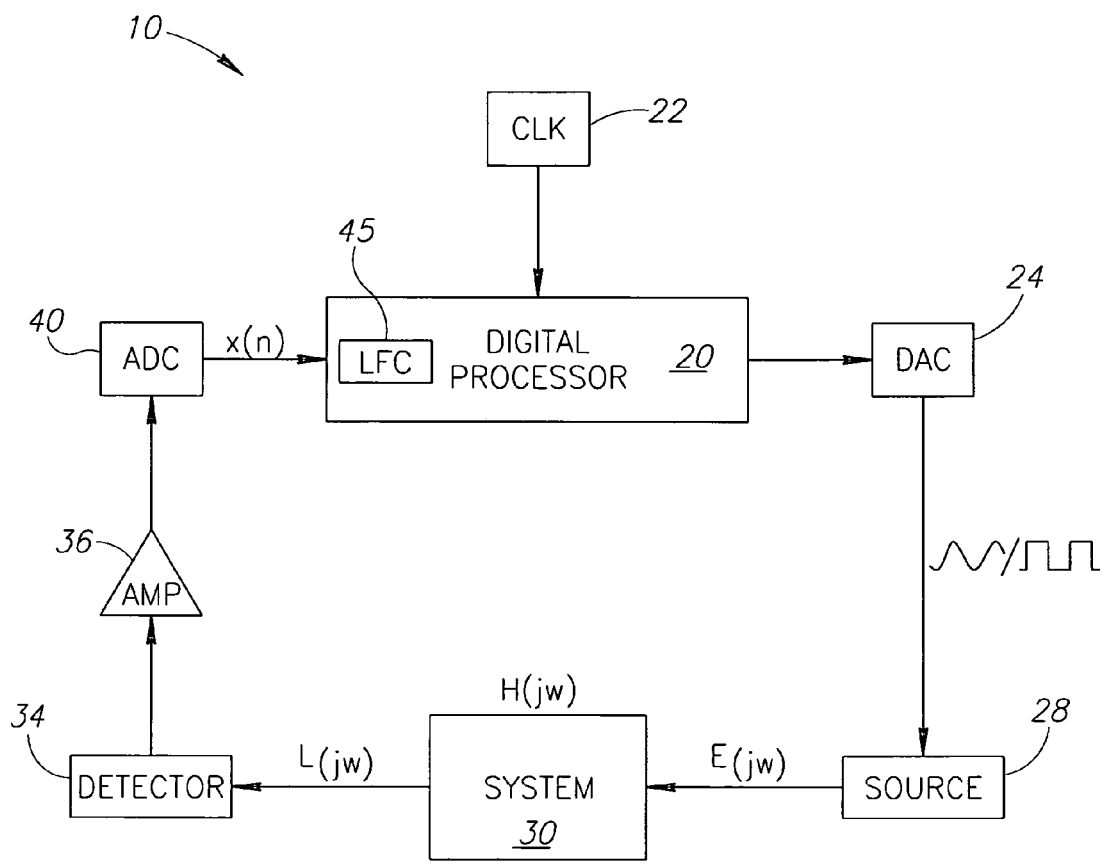
FIG. 1 is a schematic diagram of an apparatus that measures phase shift and amplitude of a system.

Attention is now directed to FIG. 1, that shows the disclosed subject matter as an apparatus (system or device) 10 including a digital processor 20, coupled with a system 30, for example, a linear or physical system. The digital processor 20 includes one or more processors, control logic, components, and the like for determining quantities and measurements, such as the phase, amplitude as well as other measurements of the system 30, as well as other quantities or measurements such as the phase shift or amplitude ratio between the input signal to the digital processor 20 and an output signal, typically output from the digital processor 20.

The apparatus 10 includes a crystal clock oscillator (CLK) 22, that, for example, runs at 1 to 25 MHz. The digital processor 20 uses the crystal clock oscillator 22 to generate a highly stable periodic signal called the "sample clock", typically at frequencies of 200 kHz or less. The sample clock signal is used to synchronize the calculation of successive numerical values of an excitation signal, such as in the form of sinusoidal waves or square waves. These signals, represented by either the sinusoidal wave or the square wave, are synchronously transferred to a digital to analog converter (DAC) 24, which transforms the samples to an electrical waveform that drives a source 28.

The source 28 is, for example, a transducer that receives electrical signals (typically as waves or waveforms) from the DAC 24, and converts it into corresponding modulated excitation light or energy, depending on the specific system 30.

For example, when the system 30 includes a luminescent probe molecule or other luminescent material, the source 28 typically includes one or more light emitting diodes (LEDs). Alternately, when the system 30 includes a sample with electrical impedance characteristics, the source emits electric energy (signals) from an electrode, Radio Frequency (RF) energy from an antenna, or magnetic energy (signals) from an inductance coil.

The emitted energy or light from the system 30, is received by a detector 34, that typically includes a transducer. The transducer includes a receiver, such as a photodiode(s) for receiving light, an electrode, for electricity, an antenna, for radio frequency, or a coil, for magnetic energy, coupled with a converter, that converts the received light or energy (electric, radio frequency or magnetic) to an output, typically electrical signals. These electrical signals may be amplified by an amplifier (AMP) 36, prior to being received by an analog to digital converter (ADC) 40. The process of conversion of the electrical signal to digital data in the ADC 40 is synchronized to the crystal clock oscillator 22.

Figure 2A:
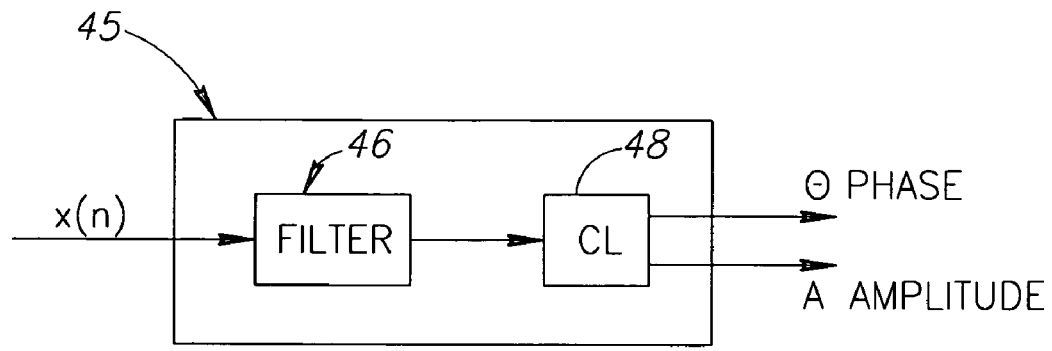
FIG. 2A is a block diagram of the linear filter component of the digital processor that performs a modified Goertzel Algorithm.
Figure 2B:
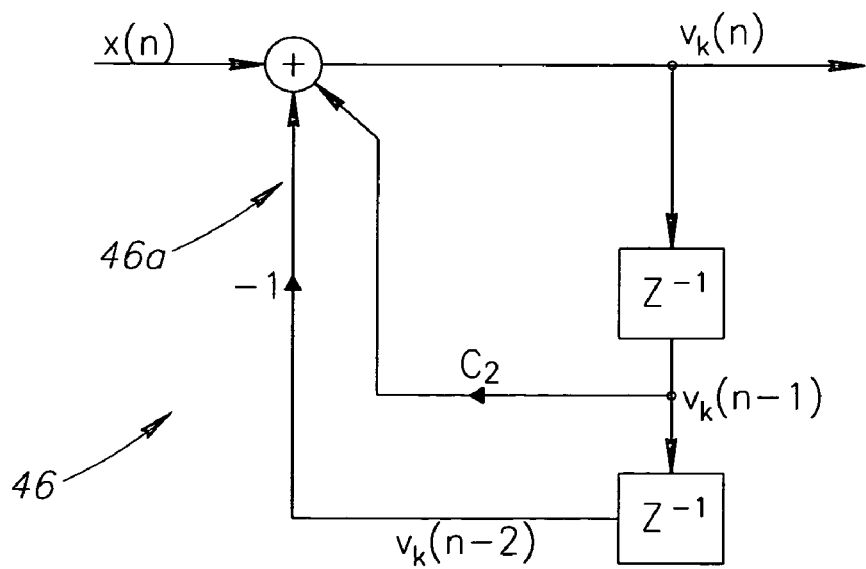
FIG. 2B is a diagram of a flow graph for an IIR filter, in the digital apparatus of FIG. 1.

The ADC 40 sends digital data to the digital processor 20. This digital data (typically in signals corresponding to waves or waveforms) is input into the linear filter component (LFC) 45, formed of a filter 46 and control logic (CL) 48 (e.g., one or more processors), as shown in FIG. 2A. The filter 46 is, for example, a linear filter, such as a second order filter (e.g., a second order digital filter or second order digital resonator), and, for example, an Infinite Impulse Response (IIR) filter 46a. The IIR filter, is, for example, a modified Goertzel filter, as shown in FIG. 2B.

Figure 3:
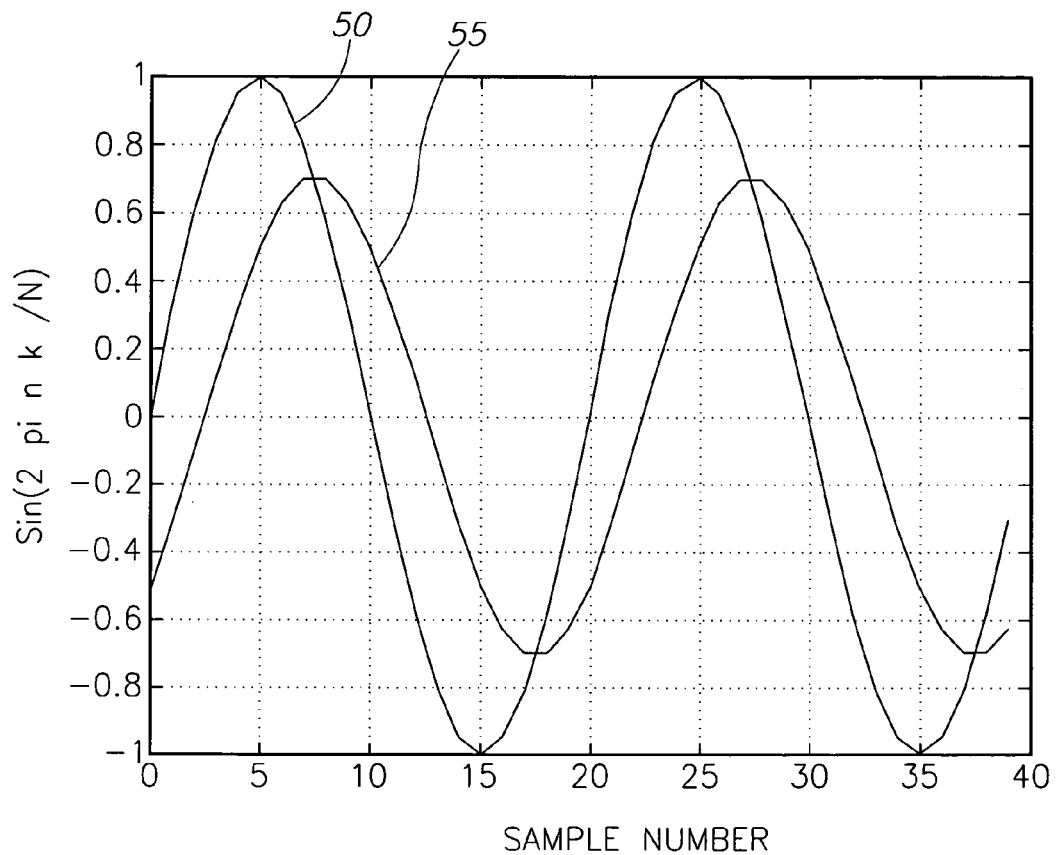
FIG. 3 is a diagram of excitation and emission two waveforms associated with the apparatus of FIG. 1.

The output from the linear filter component 45 is used to determine the phase shift, expressed as $\Delta\theta$, between the input waveform (50 of FIG. 3) to the system 30 and the output waveform (55 of FIG. 3) of the system 30, as described below. In FIG. 3, the points of sampling on the input waveform 50 and the output waveform 55 occur at integral sample number intervals. The process described below not only measures the phase shift of the system 30, expressed as $\Delta\theta$, but also of the phase shift contributions of the DAC 24, Source 28, detector 34, amplifier 36, ADC 40 and any digitally induced phase delays from the Digital Processor 20.

Should it be desired to determine the phase shift of the system 30, separate from the phase shift contributions of the components, the phase shift of the system 10, expressed as $\Delta\theta$, is measured using a system 30 of known phase shift, expressed as $\phi$, and the measured phase $\theta$, from the system 30. Subsequent measurements of phase $\theta$ then are corrected with the stored value(s) to obtain only the phase shift due to the system 30.

Phase and Amplitude Determination

The processing of the signal(s) by the linear filter component 45 in the Digital Processor 20 (or peripheral thereto) are now detailed. The system 30 for which this signal processing is described, for example, is a luminescent probe, although R/C, Radio Frequency and magnetic systems, as detailed above, are also suitable, with modifications made to the apparatus 10, to accommodate the type of system 30, being well known to those skilled in the art. The second order digital filter receives an input signal(s) (in the apparatus 10 from the ADC 40) and produces an output signal(s), that is used to calculate the phase shift and amplitude ratio of the luminescent probe.

The second order linear filter, is typically an infinite impulse response (IIR) filter 46a (FIG. 2B). This IIR filter 46a, as shown in FIG. 2B, filters the received input signal(s), and the filter output is used by control logic (CL) 48 to compute the amplitude and phase of the input signal to the digital processor 20, in order to calculate the amplitude ratio and phase shift of the luminescent probe (linear system) from which the requisite measurement or quantity is determined.

With the system 30 being a luminescent probe, the luminescence can be modeled with a transfer function, expressed as H(jw) describing the amplitude and phase response of the emission of the luminescent probe in response to excitation energy. The general description of the system 30 is expressed in Equation 1 (Eq. 1) as:

$$L(jw)=H(jw)E(jw) \qquad \text{Eq. 1}$$

where,

E(jw) is the input excitation light wave, and,

L(jw) is the output luminescent emission.

The transfer function H(jw) is defined in Equation 2 as:

$$H(jw)=A(w)\angle\theta(w)=R(w)+jI(w) \qquad \text{Eq. 2}$$

The properties of the transfer function H(jw) are expressed in polar and rectangular coordinates. In the polar representation A(w) is the amplitude at frequency w, and $\theta(w)$ is the phase shift at frequency w. In rectangular coordinates R(w) is the real part and I(w) is the imaginary part, both being functions of the frequency. For example, the phase shift at a certain frequency may be related to oxygen or other analyte concentration.

The second order linear filter 46 of FIG. 2A, specifically as an IIR filter 46a, is shown schematically in FIG. 2B, to which attention is also directed. The IIR filter 46a operates on N samples sequentially, typically in real time, where "N" represents a finite number of samples. Also, in FIG. 2B, the boxes with $Z^{-1}$ reference a delay element, here, a delay by one sample point, and the circled "+" is a summation.

The output of the IIR filter 46a is used to obtain a phase shift, expressed as $\Delta\theta$, and an amplitude measurement, expressed as $A_R$, on the luminescent sample of the system 30, as follows. The digital processor 20 causes the source 28 to output an excitation light wave that is modulated at a known frequency, for a finite period of time during which the excitation modulation cycles of either a sinusoid or square wave are generated. The resulting emissions of the system 30 are converted into N samples by the ADC 40, and are processed by the second order filter 46 (e.g., the IIR filter 46a) in the digital processor 20. After filtering N samples, the LED or other excitation source 28 is turned off and the linear filter operation is halted.

Figure 4A:
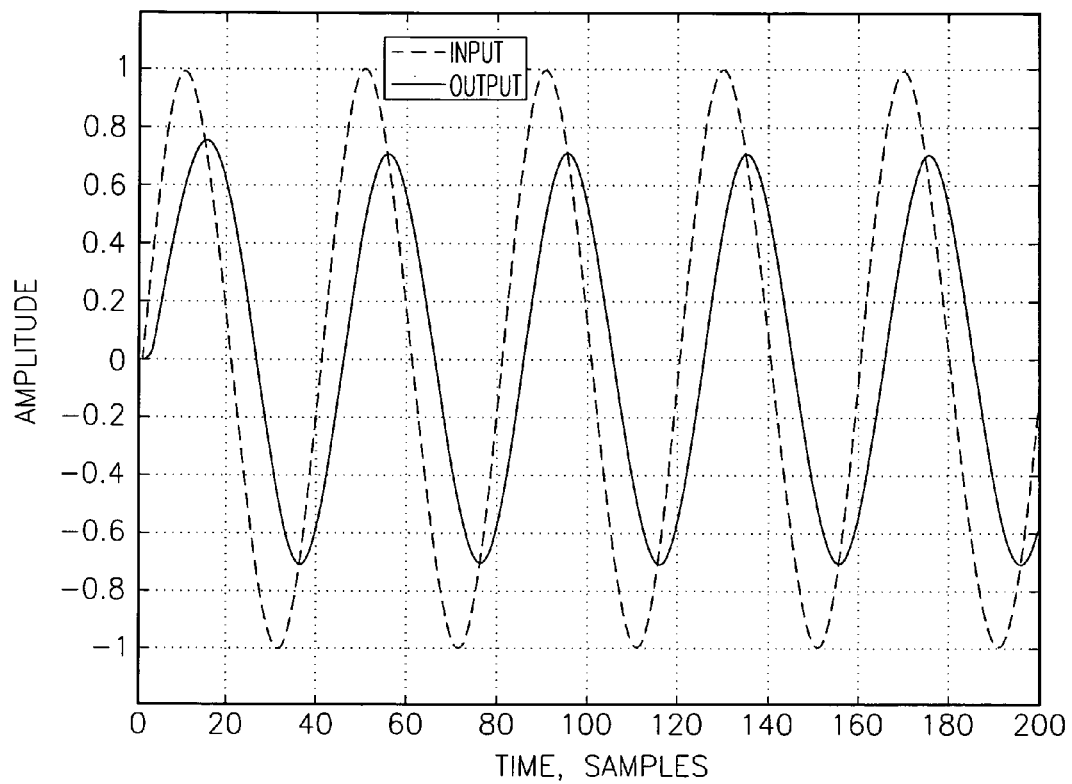
FIG. 4A is a diagram of inputs and outputs of the system of the system of FIG. 1 with sine wave input.
Figure 5A:
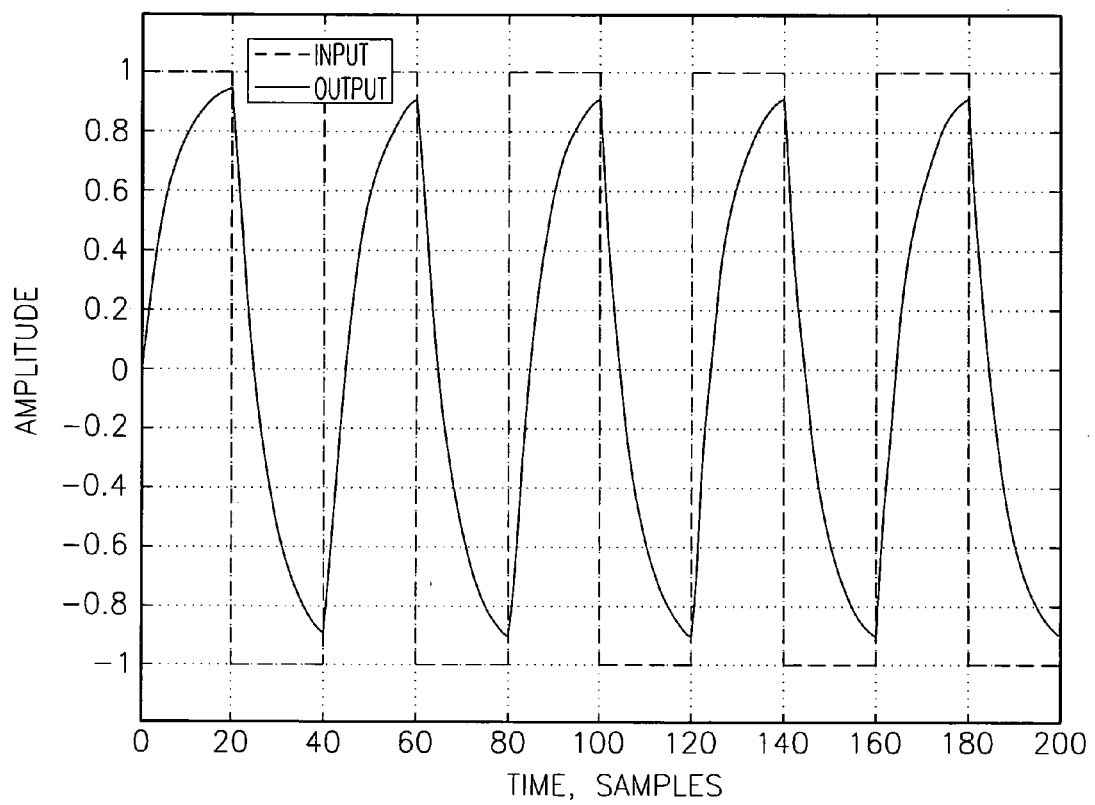
FIG. 5A is a diagram of inputs and outputs of the system of FIG. 1, with square wave input.

A graphical representation of the data from the ADC 40 and the digital processor 20 is shown in FIG. 4A, for an input sinusoidal wave, and in FIG. 5A, for an input square wave, and includes N discrete samples, and k excitation cycles, in both FIGS. 4A and 5A, five cycles. Each time a sampled data point, x(n), is received from the ADC 40, the following computation is made to implement the IIR filter 46a. This computation is Equation 3 (Eq. 3), that makes reference to FIG. 2B, and is expressed as:

$$v_k(n)=C_2 v_k(n-1)-v_k(n-2)+x(n) \qquad \text{Eq. 3}$$

where $v_k(n)$=recursive filter output x(n)=real $n^{th}$ input value $v_k(n-1)$=delay line element 1 (delayed by 1 sample)

$v_k(n-2)$=delay line element 2 (delayed by 2 samples)

$$C_2 = 2\cos\frac{2\pi k}{N}$$

N=number of samples per data set; and, k=number of cycles of the excitation light wave, which is related to the frequency at which the excitation light wave is modulated.

The relationship between k, N, $f_{mod}$ and $f_{sample}$ is k/N=$f_{mod}$/$f_{sample}$, where $f_{mod}$ is the modulation frequency and $f_{sample}$ is the sample rate. The initial conditions on the IIR filter 46a are $v_k(-1)=v_k(-2)=0$.

Figure 4B:
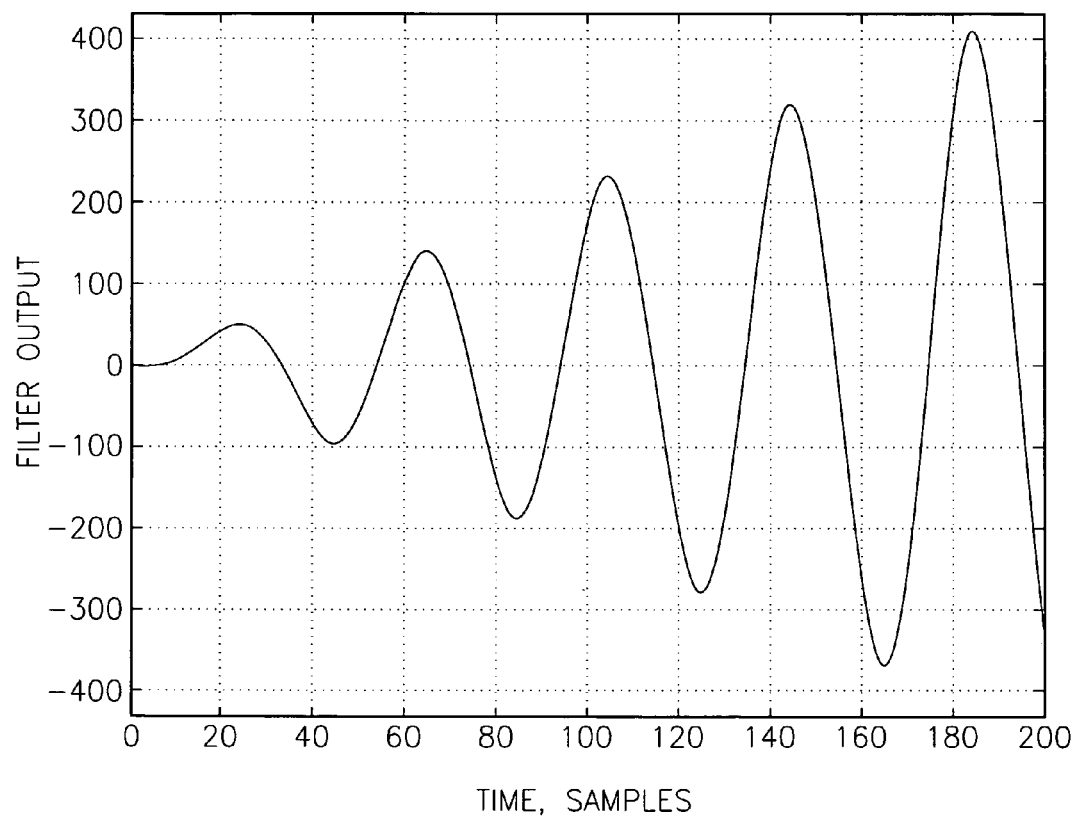
FIG. 4B is a diagram of an output signal of the modified Goertzel filter of FIG. 2B that filters the output from FIG. 4A.
Figure 5B:
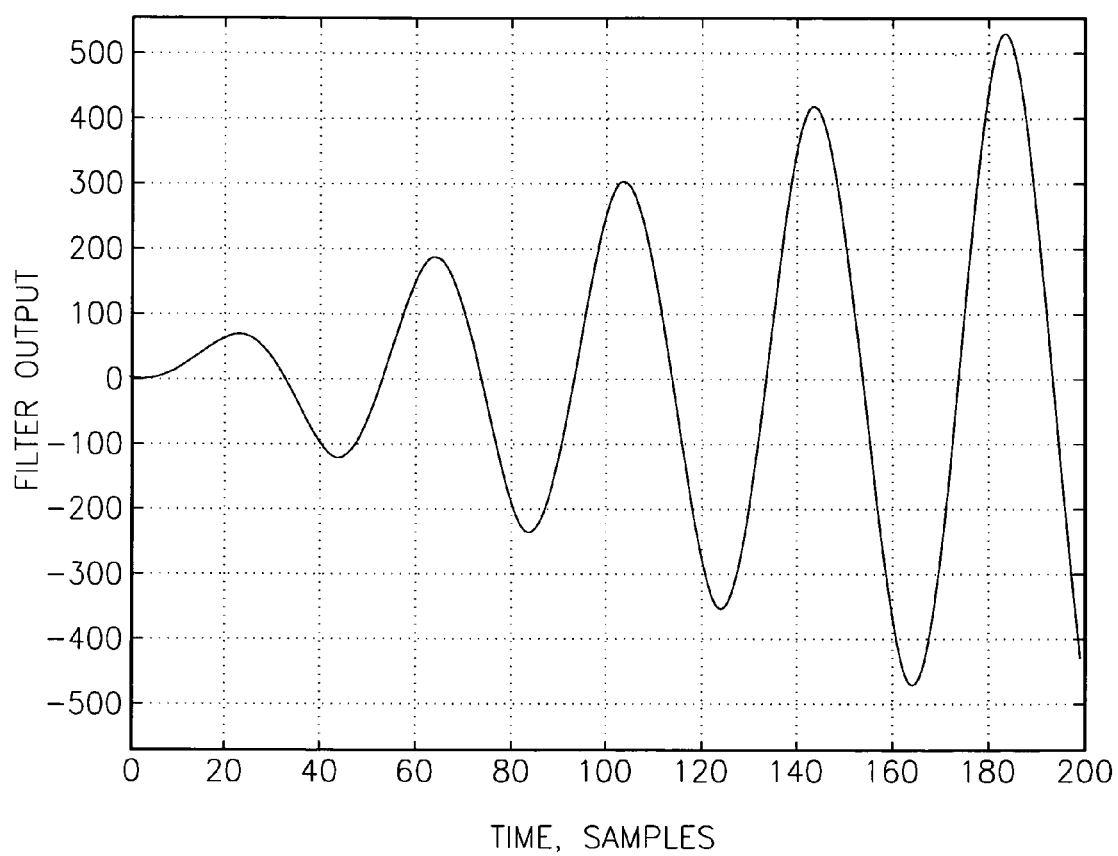
FIG. 5B is a diagram of an output signal of the modified Goertzel Filter of FIG. 2B that filters output from FIG. 5A.

Turning also to FIG. 4B and FIG. 5B, there is shown graphically the output of the IIR filter 46a, expressed as $v_k(n)$, over N samples, for both sinusoidal wave excitation (FIG. 4A) and square wave excitation (FIG. 5A). After N samples are received and linearly filtered according to Equation 3 (Eq. 3), the real component R(w) and the imaginary component I(w) of the transfer function H(jw) of Equation 2 (Eq. 2) are calculated as Equation 4 and Equation 5, respectively, as follows:

$$R(w)=v_k(N)-C_1 v_k(N-1) \qquad \text{Eq. 4}$$

$$I(w)=S_1 v_k(N-1) \qquad \text{Eq. 5}$$

where the constants of $C_1$, and $S_1$ are expressed as:

$$C_1 = \cos\frac{2\pi k}{N}$$

and $$S_1 = \sin\frac{2\pi k}{N}$$

The quantities of $C_1$, $C_2$ and $S_1$ can be precomputed based on the known values of N and k. Recalling that k is the number of excitation cycles per data set, and N=number of converted samples per data set, it can be seen that the ratio k/N does not change as the time during which the excitation source, or light source in the case of a luminescent system, is activated. Instead, it can be written as $f_{mod}/f_{sample}$. Thus these coefficients only need to be recalculated when changing sampling frequency in the ADC 40, and/or excitation modulation frequency.

The phase and amplitude of the signal x(n) is computed as follows:

Depending on the signs of R(w) and I(w) the phase, expressed as θ, is calculated using one of the following equations of the "6" Series, or Equations 6.1-6.6, as follows:

where R(w)>0 and I(w)>0

$$\theta=\arctan(I(w)/R(w)) \qquad \text{Eq. 6.1}$$

where R(w)>0 and I(w)<0

$$\theta=\arctan(I(w)/R(w)) \qquad \text{Eq. 6.2}$$

where R(w)<0 and I(w)>0

$$\theta=180+\arctan(I(w)/R(w)) \qquad \text{Eq. 6.3}$$

where R(w)<0 and I(w)<0

$$\theta=\arctan(I(w)/R(w))-180 \qquad \text{Eq. 6.4}$$

where R(w)=0

$$\theta=90 \qquad \text{Eq. 6.5}$$

where I(w)=0

$$\theta=0 \qquad \text{Eq. 6.6}$$

The arctangent (arctan) may be implemented via a look up table, using a polynomial approximation or by using a software library function compatible with the specific Digital Processor 20, as provided by the compiler manufacturer. Suitable low power Digital Processors, for implementing the Second Order Filter Algorithm (the modified Goertzel Algorithm) in the linear filter component 45, include, for example, the MSP430F427 or the MSP430F4270 processors, from Texas Instruments.

The amplitude, expressed as A(w), is calculated using the following equation $$A(w)=\sqrt{I(w)^2+R(w)^2} \qquad \text{Eq. 7}$$

This Amplitude A(w) is now expressed as the obtained amplitude ($A_1$) in accordance with the amplitude "A" above, to continue the exemplary calculations.

The obtained phase θ and amplitude $A_1$ are now used to determine the phase shift Δθ and the Amplitude ratio of the luminescent sample $A_R$, to obtain the requisite quantity, measurement or the like.

Phase shift Δθ is expressed by the equation:

$$\Delta\theta=\theta-\phi \qquad \text{Eq. 8.1}$$

where, θ is the measured or obtained phase of the input signal from the ADC 40 to the processor 20, as detailed above; and, φ is the phase of the output from the digital processor 20 that goes to the DAC 24.

In the apparatus 10 of FIG. 1, the reference phase is zero, such that φ=0, and the phase shift equation (Eq. 8.1) becomes:

$$\Delta\theta=\theta$$

where the phase shift is the measured or obtained phase. This phase shift may then be compared against known quantities or measurements, to obtain the requisite value, such as the amount of an analyte present in a material. In many cases Δθ is sufficiently close to the phase shift through sample 30 to be used without further correction.

Amplitude ratio $A_R$ is expressed by the equation:

$$A_R=A_1/A_O \qquad \text{Eq. 8.2}$$

where, $A_1$ is the measured or obtained amplitude of the input signal to the processor 20, as detailed above; and, $A_O$ is the amplitude of the output of 20, defined to be 1.

In the apparatus 10 of FIG. 1, the amplitude of output from 20 is one, such that $A_O=1$, and Equation 8.2 becomes:

$$A_R=A_1,$$

where the amplitude ratio is the measured or obtained amplitude. This amplitude ratio may then be compared against known quantities or measurements, to obtain the requisite value, such as the amount of an analyte present in a material.

When certain conditions are met, the IIR filter process can be further simplified. If the values of k and N are chosen such that the ratio of k/N equals ¼, the $C_2$ coefficient equals zero. Then the IIR filter equation, Equation 3 above, becomes Equation 3.1, expressed as:

$$v_k(n)=x(n)-v_k(n-2) \qquad \text{Eq. 3.1}$$

With Equation 3.1, replacing Equation 3, the processes for determining phase θ, and amplitude $A_1$ uses Equations 4-7, as detailed above.

In this case, there are not any multiplications needed to implement the IIR filter. This optimization greatly simplifies the IIR filter computation. Multiplications are more time consuming than additions on digital processors that do not have a fixed or floating point hardware multiplier. Table 1, immediately below, shows the computational complexity of the IIR filter, for M frequency bins, one frequency bin at an arbitrary frequency and one frequency bin when the filter coefficient equals zero, that is when k/N equals ¼.

TABLE 1

Table 1. Real-Time computational complexity of IIR Filter

| | M Frequency Bins | | One Frequency Bin | | One Frequency Bin at ¼ $F_s$ | |
|---|---|---|---|---|---|---|
| | Multiplies | Adds | Multiplies | Adds | Multiplies | Adds |
| IIR | MN | 2MN | N | 2N | 0 | N |

Infinite Impulse Response (IIR) Filters

The data sequence x(n) is shown in FIG. 4A as a solid line. FIG. 4B shows the evolution of the second order IIR Filter output quantity $v_k$. This quantity is the output of IIR Filter 46 and is used by the control logic 48 to compute phase and amplitude. The dynamic range of magnitude of this quantity $v_k$ will determine the size and type (fixed or floating point) of the variables needed in the calculation. In the present example, the signal waveform submitted to the IIR filter has a peak value of 0.705, as shown in FIG. 4A as a solid line. For the given frequency and 200 samples, the maximum amplitude (absolute value) reached by $v_k$, the output of the IIR filter, is 411, as shown in FIG. 4B. Digital resonant filters, such as the IIR filter employing at least a portion of the modified Goertzel algorithm, with poles on the unit circle behave in this manner, where the output grows without bounds.

Thus there is an increase by a factor of over 400 in the numerical magnitude at the output of the IIR filter. This increase is linear in number of samples, N, and also depends on the ADC, for example ADC 40, sample frequency. The frequency dependence is more complicated, producing significantly larger numerical magnitudes for frequencies close to zero and close to the Nyquist frequency than for frequencies close to half the Nyquist frequency. The Nyquist frequency, as used throughout this document, is defined to be half of the sample rate. If a fixed point processor is used to perform the IIR filter, care must be taken to select a variable width that will accommodate the maximum expected filter output, as determined by the number of samples N and the ADC sampling frequency, without overflowing. If a processor employing floating-point calculations is used instead of fixed-point, the growth in the magnitude of $v_k$ becomes trivial, so as to be negligible.

In the ideal case, the IIR filter will operate on a sampled stream of data, the length of which set will contain: 1) an exact integral number of samples, N, and 2) an exact integral number of excitation signal cycles, k. It is not necessary that the number of samples per excitation signal cycle be integral. For instance, three signal cycles in 50 samples (or 3,000 cycles in 50,000 samples) produces an exactly correct phase measurement, within arithmetic precision, even though there are 16⅔ samples per excitation signal cycle.

In the more usual approach, the ADC sampling rate will be specified in Hertz (Hz) and fixed, while the modulation frequency of the excitation source, and the duration over which N samples are converted, (defined as the excitation source on time, expressed as $t_{on}$) will be set as needed for particular measurement conditions. For example, for the following parameter set:

ADC Sampling frequency, $f_{sample}$=48 kHz
Excitation Modulation frequency, $f_{mod}$=10 kHz
Excitation waveform: sinusoidal
Excitation source on time $t_{on}$=0.01 second
Total Phase shift through luminescent system and device: 23 degrees In this example, there will be N=0.01*48,000=480 samples per data set and k=0.01*10,000=100 signal cycles per data set. Because both of these products are exactly integral, the phase calculated using the output of the second order filter result will be exact.

$$k = \frac{f_{mod}}{f_{sample}} N = \frac{10k}{48k} 480 = 100$$

With these parameters, the coefficients are: C1=0.258819045, S1=−0.9659258262, C2=0.5176380902. After the IIR filter has been propagated, the last two calculations are shown below, to illustrate the final computation of phase (θ), as:

Real=195.794103147847−C1*(−97.083511264731)
    =220.921164818631

Imag=S1*(−97.083511264731)=93.7754708287823 where, $$\theta = \arctan\left(\frac{93.775470828}{220.92116481}\right) * \frac{180}{\pi} = 23°$$

The phase shift (Δθ, as detailed above), is the difference of the measured phase of the input signal from the ADC to processor 20 (expressed as θ) and the phase (φ) of the output signal of processor 20, as detailed above in Equation 8.1, and provides a value used to characterize the luminescent system's response at 10 KHz. Excitation modulation frequency and phase shift may be used to calculate a luminescent lifetime, or phase shift, related to analyte concentration.

Figure 6:
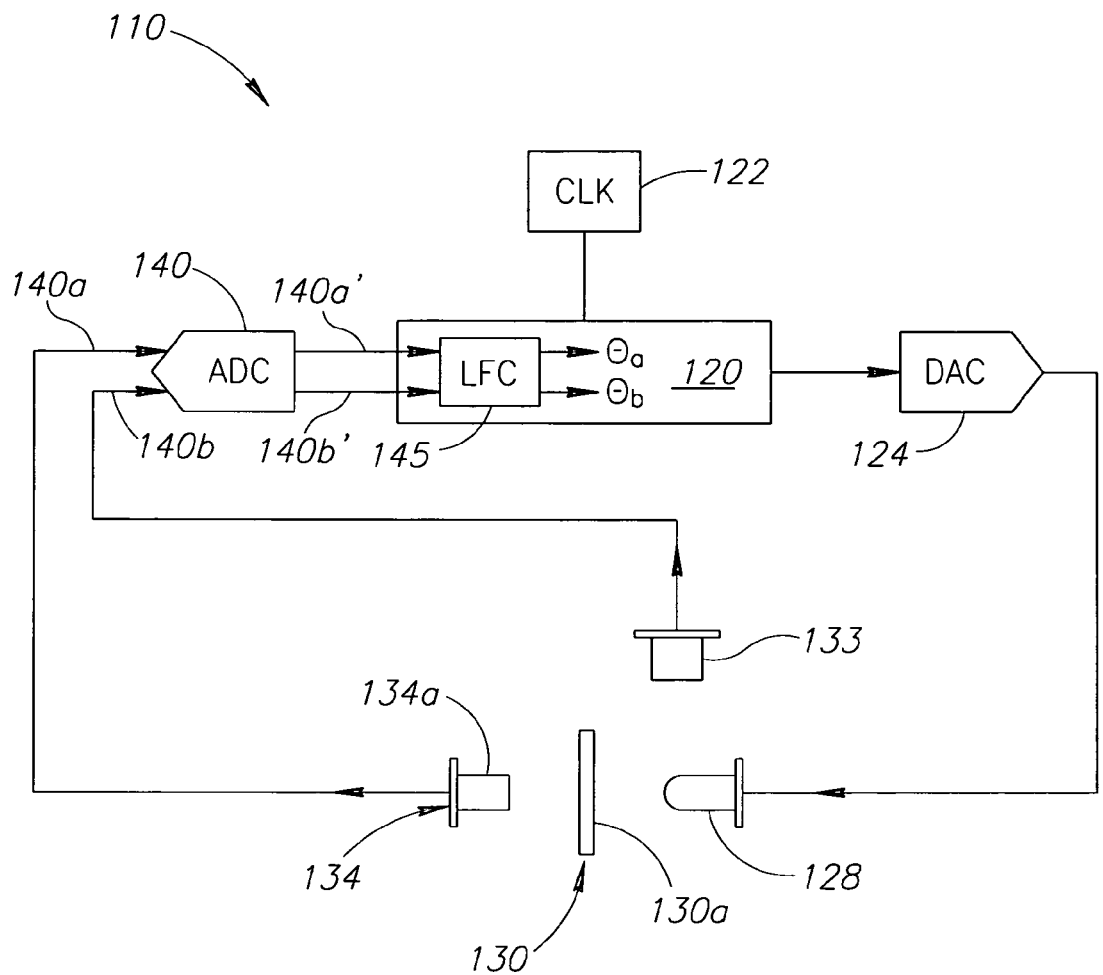
FIG. 6 is a diagram of another embodiment of phase and amplitude measurement device.

Attention is now directed to FIG. 6, where there is shown an apparatus 110, that uses linear filters of the disclosed subject matter to make differential phase measurements for compensation of unwanted phase delay.

In this apparatus 110, as well as the apparatus 210, 310 and 410 detailed below, identical or similar components, that have been previously discussed above for the apparatus 10 of FIG. 1, will be identified with the same numerals, increased by "100" in each succeeding apparatus. These elements, with numerals increased by "100" for each succeeding apparatus, take the descriptions of the elements, whose numbering was increased by "100." Additional description is provided where necessary, and additional elements are described where necessary, for understanding of the disclosed subject matter.

The apparatus 110 includes a digital processor 120. A linear filter component (LFC) 145, similar to the linear filter component 45 detailed above, is implemented in the digital processor 120 (it may also be peripheral thereto). The digital processor 120 is in communication with a digital to analog converter (DAC) 124, that functions to convert digital to analog signals. The DAC 124 drives a source 128, for example, a light emitting diode (LED), that typically emits blue light, as the excitation light. The system 130, for example, includes a luminescent or fluorescent probe 130a, on which the excitation light is transferred from the source 128.

A first photodiode 133, that also forms part of a detector, the detector also being a transducer, is used to monitor the excitation light emitted directly from the source 128. A detector 134, that includes a photodiode 134a (second photodiode), the detector 134 also including a transducer, serves to detect the luminescent light emitted from the luminescent sample 130a.

The output from the first photodiode 133 and the second photodiode 134a, is typically converted into signals by the respective transducers, is supplied to an analog to digital converter (ADC) 140, at the respective inputs 140a, 140b. Each of the inputs 140a, 140b defines a channel 140a', 140b'. The ADC 140, for example, is a Sigma-delta converter, such as those intended for stereo sound, as they are well suited to this application because phase delay offset (difference, skew) between the input channels is carefully controlled and minimized through symmetrical design.

In this method, the two inputs 140a, 140b to the ADC 140 will be sampled contemporaneously, typically simultaneously, and the converted data is supplied to the digital processor 120 as pairs of numbers. In the digital processor 120, in the linear filter component 145, two implementations of the second order filter algorithm (modified Goertzel Algorithm) are made in series, as described for the IIR filter 46a above. Should there be two linear filter components 145, one for each channel 140a', 140b', implementations of the second order filter algorithm (modified Goertzel Algorithm) are made in parallel.

As the system 130 is a luminescent probe 130a, the phase shift and amplitude change (expresses as the amplitude ratio $A_R$), through the probe are modeled by Equations 1 and 2, as detailed above. The IIR filters, in accordance with the IIR filter 46a of FIG. 2B, detailed above, are executed in parallel with separate delay lines, to accommodate the two separate inputted waveforms. After N samples are received over k excitation cycles and linearly filtered according to Equation 3 (Eq. 3), the real component R(w) and the imaginary component I(w) of the transfer function H(jw) of Equation 2 (Eq. 2) are calculated as Equation 4 and Equation 5, as detailed above, to determine the requisite phase ($\theta_a$ and $\theta_b$), finally calculated with the "6" series equations. For both waveforms, Equation 8.1 for phase shift, as detailed above ($\Delta\theta_a=\theta_a-\phi$ and $\Delta\theta_b=\theta_b-\phi$, is now applied, and for both waveforms, $\phi=0$, such that $\Delta\theta_a=\theta_a$ and $\Delta\theta_b=\theta_b$. As long as both IIR filters can be executed in the time between samples from the ADC 140, each of these will contain all the phase shifts contributed by the analog, digital components, and the luminescent sample of the system 130.

Accordingly, two values for phase are obtained, one for each of the waveforms, expressed as $\theta_a$, from input 140a for the system 130, and $\theta_b$, from input 140b. When the phase of input 140b ($\theta_b$) is subtracted from the phase of the input 140a ($\theta_a$), the difference will be only the sample luminescence phase shift ($\Delta\theta$), uncontaminated by system delays, either analog or digital.

The phase shift ($\Delta\theta=\theta_a-\theta_b$), as detailed above, provides a value used to characterize the luminescent system's response, and is used, for example, to calculate a luminescent lifetime, or related to analyte concentration.

In the apparatus 110, the only uncompensated phase error between the channels (which contributes directly to the phase estimate of the sample in the system 130) will be due to any difference in delay between the two photodiode-plus-preamplifier channels. The more similar these channels are made, the more exactly the calculated phase difference will represent delay due to luminescence lifetime alone. In practical systems, a procedure can be provided for measuring and subsequently subtracting any residual phase delay due to mismatch between the channels. This method is so effective that it is often sufficient merely to create a signal path from the output of the DAC 124 to the second input 140b of the ADC 140 that contains an amplifier (not shown). The amplifier roughly duplicates the phase shift of the photodiode preamplifier. As a result, residual asymmetry can be calibrated out. Exactness of measurement then becomes a function of the stability of the inter-channel difference, a second-order error.

However it is arranged, the advantages of the symmetrical dual-channel system are so great that this approach is strongly recommended in all cases, even in the absence of a second photodiode-plus-preamplifier sub-system. It should be noted that program delays and phase-offsets in the calculations will also cancel, as long as they are present in both channels and all calculations needed for input samples can be completed in the time between samples.

Practical systems will unavoidably have phase delays in the analog components, and possibly much larger delays in the data converters: the ADC and DAC. For this and other reasons, it is advisable to regard all phase measurement and calculation as determination of relative phase rather than absolute phase. That is, it is generally advantageous for the final result to be the difference between two measured phases, whether these measurements are made simultaneously or sequentially. If sigma-delta converters are used, as they commonly are, data converter phase delay can be hundreds of degrees for modulation frequencies near the Nyquist frequency limit. Because such phase delay is typically determined by the crystal-controlled system clock, data converter delay is of a digital nature and usually quite stable. In these circumstances it may be possible to eliminate it through programming, but it is far simpler and more general to remove delays through some form of symmetrical dual-channel approach.

Apparatus for Phase Correction

Figure 7:
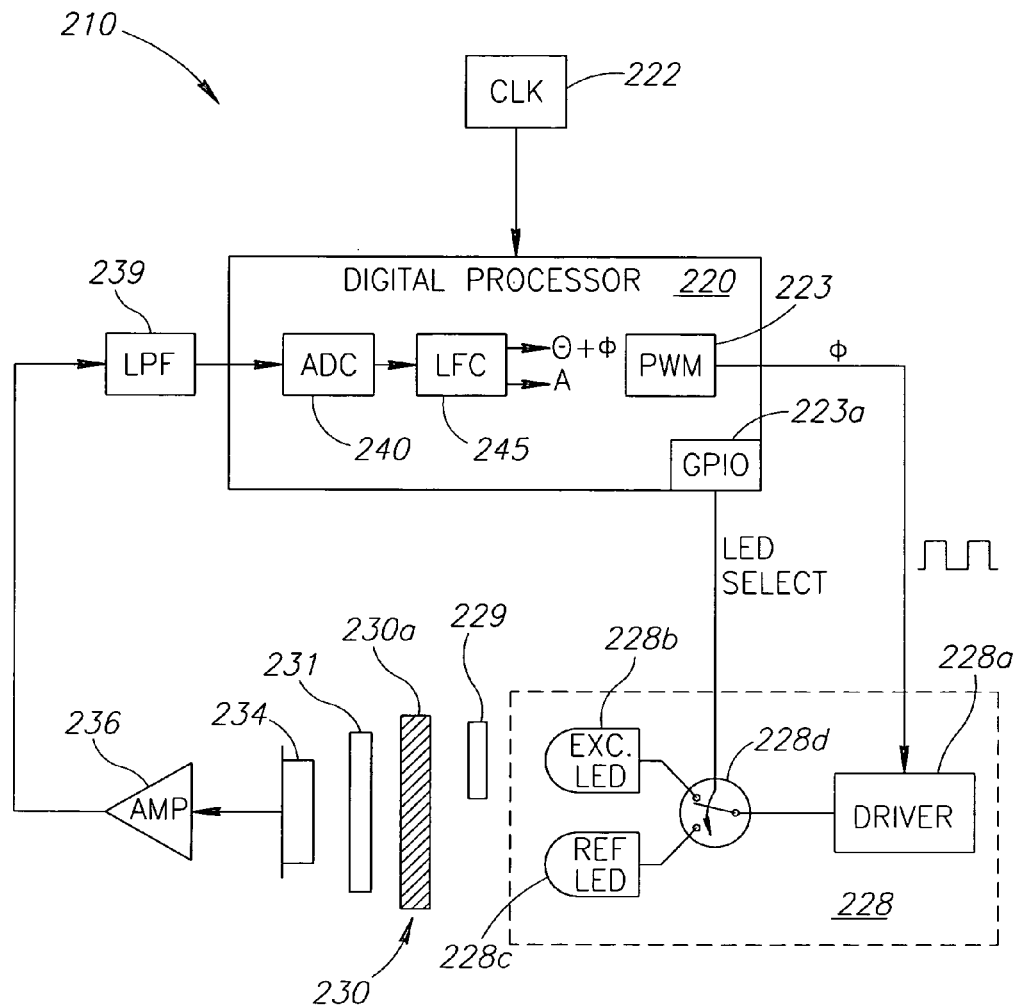
FIG. 7 is a diagram of another embodiment of a phase and amplitude measurement apparatus.

FIG. 7 shows an apparatus 210 that uses second order filters of the disclosed subject matter, and makes differential phase measurements, for compensation of unwanted phase delays. The apparatus 210 includes a digital processor 220, for example, a microcontroller, the digital processor 220 implementing a linear filter component 245, similar to the linear filter components 45 and 145 detailed above. The digital processor 220 is electrically coupled to a crystal oscillator clock (CLK) 222. The digital processor 220 typically includes an on-chip pulse width modulator (PWM) 223, that, for example, outputs a 50% duty cycle square wave to a driver 228a, the square wave modulating the driver 228a, that in turn modulates one of two selectable LEDs 228b, 228c (by a switch 228d, controlled by a general purpose input/output (GIPO) 223a) at a fixed frequency. The driver 228a, selectable LEDs 228b, 228c and switch 228d, define a source 228 (as shown in the broken line box), similar to the sources 28, 128, detailed above.

The driver 228a changes a voltage source waveform, for example, a square wave, into a current source waveform used for exciting the LEDs 228b, 228c. The excitation LED 228b has a short wavelength spectral output, such as an ultraviolet (UV), blue or green LED, that is used to excite a luminescent sample 230a, defining the requisite system 230.

An optical filter 229 is used to improve the spectral purity of the LED 228b, and eliminate wavelengths of light that overlap the emission spectrum of the luminescent sample 230. The choice of the excitation LED 228b is dependent on the absorption peak of the luminescent sample 230a of the system 230, and is known to those of skill in the art. An optical filter 231 is placed in front of the detector 234 to block light from the first or excitation LED 228b.

The second LED 228c is a reference LED. It has a spectral output of longer wavelengths, such that it does not substantially excite emission luminescence in the sample 230a. Instead the reference LED 228c feeds directly through the system 230 or is scattered before it impinges on the detector 234 (the detector 234, for example, a photodiode, such as a P intrinsic N (PIN) photodiode). As a result, the light from the second or reference LED 228c provides a reference phase measurement to cancel out unwanted phases of the components of the apparatus 210.

The reference LED 228c is time-division-multiplexed with the excitation LED 228b. This reference phase measurement removes phase shifts due to the photodiode (of the detector 234), amplifier 236, low-pass filter (LPF) 239 and sampling process. The spectral output of the reference LED 228c is not critical, except that it overlaps (at least partially) the emission of the luminescent sample 230a and is detectable by the detector 234.

A preamplifier 236 amplifies the electrical signal from the photodiode of the detector 234 (the detector 234 also includes a transducer like the detectors 34 and 134 described above, that converts the detected emissions to electrical signals or the like), and passes it to a low pass filter 239. The low pass filter (LPF) 239 removes high frequency components to prevent aliasing in the ADC 240. For example, the microcontroller has a sigma-delta ADC 240, which samples the input signal synchronous with the operation of the PWM 223. This is easily achieved because the same clock, for example, the crystal oscillator 222, provided to the apparatus 210 is used to clock the ADC 240 and the PWM 223. This is particularly useful if the reference LED 228c is not used, the PWM modulation waveform remains phase locked to the ADC 240. The accuracy of the crystal oscillator clock 222 is important in order to prevent excitation frequencies from changing and translating into errors in the measured phase. Variations in the excitation frequency even as much as 100 Hz can cause measurable changes in the phase. The signal from the ADC 240 is received in the linear filter component 245, where it is processed, for example, to determine phase and/or amplitude, as detailed below.

As the system 230 is a luminescent probe, the phase shift of the luminescent sample 230a, represented as $\Delta\theta$, is computed by making two phase measurements, one with the excitation LED 228b, known as the total phase and expressed as $\theta_{total}$, and a phase measurement from reference LED 228c, known as the reference phase, expressed as $\theta_{ref}$. Both phase shifts are modeled by Equations 1 and 2, as detailed above.

The IIR filters, in accordance with the IIR filter 46a of FIG. 2B, detailed above, are executed in series, based on the LED 228b or 228c, that is active, to accommodate the two separate inputted waveforms. After N samples are received over k excitation cycles and linearly filtered according to Equation 3 (Eq. 3), the real component R(w) and the imaginary component I(w) of the transfer function H(jw) of Equation 2 (Eq. 2) are calculated as Equation 4 and Equation 5, as detailed above, to determine the requisite phases ($\theta_{total}$ and $\theta_{ref}$), each phase, $\theta_{total}$ and $\theta_{ref}$ calculated with the "6" series equations. For both waveforms, Equation 8.1, as detailed above, is now applied, and for both pairs of waveforms, $\phi$ in each waveform pair, is an unknown value, not equal to zero, but is the same for both waveforms. Accordingly, Equation 8.1 for each waveform pair, is expressed as:

$$\Delta\theta_{total} = \theta_{total} - \phi \qquad \text{Eq. 8.1.1}$$

$$\Delta\theta_{ref} = \theta_{ref} - \phi \qquad \text{Eq. 8.1.2}$$

The equation to determine the phase shift for the system 230 is expressed as Equation 9.1, as:

$$\Delta\theta = \Delta\theta_{total} - \Delta\theta_{ref} \qquad \text{Eq. 9.1}$$

whereby the phase shift for the system 230 ($\Delta\theta$) is expressed as, Equation 9.2, as:

$$\Delta\theta = \theta_{total} - \theta_{ref} \qquad \text{Eq. 9.2}$$

as the $\phi$ components for each waveform pair cancel each other.

As long as the IIR filters can execute in the time between samples from the ADC 140, each of these will contain all the phase shifts contributed by the analog, digital components, and the luminescent sample of the system 230. The difference in the phase shifts will be only the sample luminescence phase shift ($\Delta\theta$), uncontaminated by system delays, either analog or digital.

The phase shift ($\Delta\theta = \theta_{total} - \theta_{ref}$), as detailed above, provides a value used to characterize the luminescent system's response, and is used, for example, to calculate a luminescent lifetime, or related to analyte concentration.

An exemplary operation of the digital processor 220 is now described, with the following parameters that allow for an excitation frequency of 5208.333 Hz. The requisite parameters are as follows:

Crystal Oscillator Frequency: 8 MHz
ADC Sample Rate ($F_s$): 31.250 kHz
Total Samples (N): 1002
Frequency Index (k): 167
Excitation Frequency ($f_{mod}$): 167/1002*Fs=5208.333 Hz
Second Order Filter Coefficient:

$$C_2 = 2\cos\left(\frac{2\pi k}{N}\right) = 2\cos\left(\frac{\pi}{3}\right) = 1$$

Second Order Filter:

$$v_{167}(n) = v_{167}(n-1) - v_{167}(n-2) + x(n)$$

With this ratio of k/N=1/6, the real-time Second Order Filter Coefficient is equal to one. This filter thus requires two additions and no multiplications.

In some systems, if the modulation frequencies are sufficiently low, for example, 1 KHz to 20 KHz, the reference phase ($\theta_{ref}$) is negligibly small or does not change with time or temperature. In this case the system 210 is operable without the reference LED 228c, provided the output from the PWM 223 can be synchronized with the ADC 240 and the digital processor 220.

The systems 110 and 210 detailed above, samples, such that the Nyquist criterion will dictate the minimum acceptable sampling rate, typically 10 or 20 percent higher than twice the highest modulation frequency of the excitation source, for example, the respective sources 128, 228. This requirement applies equally to the rate of signal generation and the digitizing rate of the data converters, for example ADCs 140, 240.

The previously described apparatus 110, 210 use an excitation waveform that has a fundamental frequency, that is less than the Nyquist frequency of the analog-to-digital converter (ADC) 140, 240. This restricts the apparatus 110, 210 to low excitation frequencies, as higher excitation frequencies require the use of expensive high-speed ADCs. Additionally, the high speed ADCs typically do not have the same bit resolution as the lower speed ADCs.

Apparatus for Down Conversion

The disclosed subject matter provides apparatus that allow the fundamental of the excitation frequency to be greater than the Nyquist frequency of the ADCs. These apparatus are shown in FIGS. 8 and 9, and employ processes known as down conversion, and supporting structure.

Figure 8:
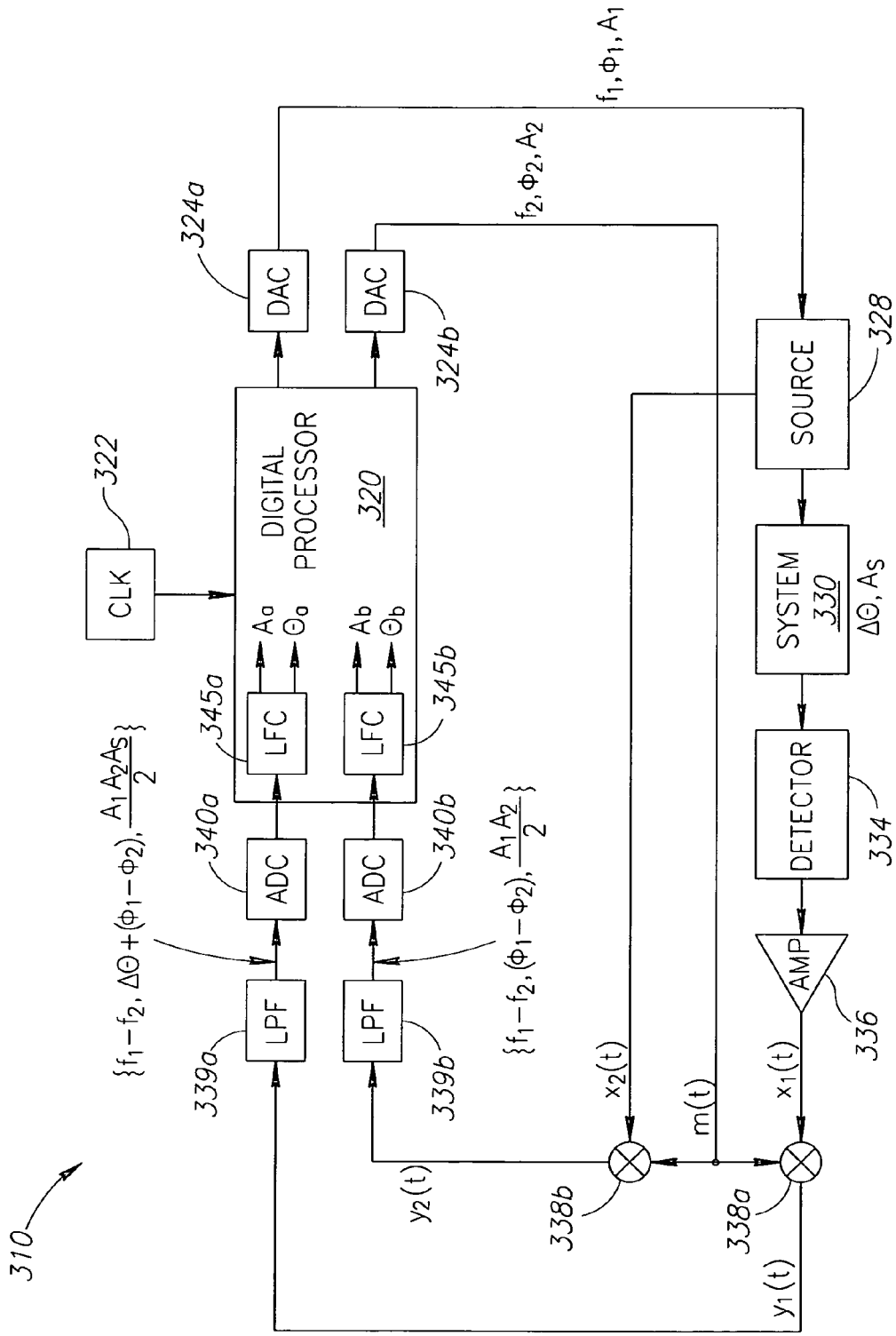
FIG. 8 is a diagram of another embodiment of a phase and amplitude measurement apparatus that performs down conversion; and, FIG. 9 is a diagram of another embodiment of phase and amplitude measurement apparatus for a luminescent probe that performs down conversion.
Figure 9:
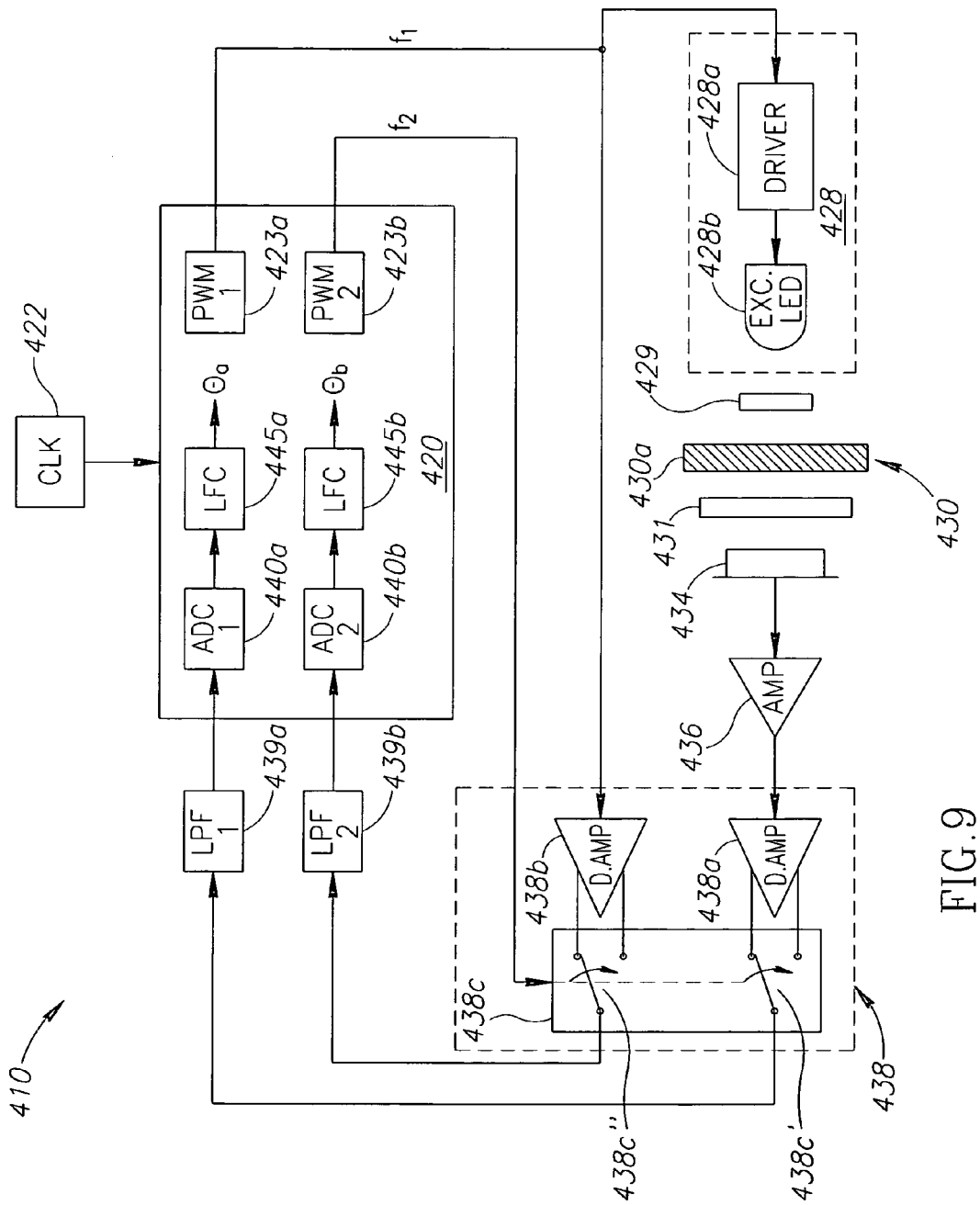

FIG. 8 shows an apparatus 310, that implements the aforementioned down-conversion process. The apparatus 310 includes a digital processor 320 with linear filter components 345a, 345b, that implement the second order linear filter algorithm (a modified Goertzel Algorithm), as described above, for the digital processor 20 of FIG. 1. The apparatus 310 employs mixers 338a, 338b, typically mixers that implement analog mixing functions, such as diode bridges, analog multipliers and Gilbert Cells. These mixers 338a and 338b, perform the down converting functions, detailed below.

A first mixer 338a, receives output from the system 330, via the detector 334 (the detector 334 also includes a transducer like the detectors 34, 134 and 234 described above, that converts the detected emissions, signals or the like, to electrical signals or the like), and amplifier 336, as well as output from a second digital to analog converter (DAC) 324b. This second DAC 324b, for example, may be a one-bit pulse width modulator, to produce a square wave, or a high speed, for example, 0 Hz to 1 GHz Direct Digital Synthesis (DDS) component. A second mixer 338b receives output from the source 328 (the source 328 may be any of the sources detailed for the source 28 of FIG. 1 above, with a light emitting diode being typical), as well as output from a second digital to analog converter (DAC) 324b, as detailed immediately below.

The apparatus 310 performs a method, where the digital processor 320, generates a waveform at first frequency ($f_1$), having phase of $\phi_1$ and amplitude of $A_1$, for digital to analog converter (DAC) 324a, on a first channel, and a waveform at second frequency ($f_2$), having phase of $\phi_2$ and amplitude of $A_2$, for a second DAC 324b. This first DAC 324a, for example, may be a one-bit pulse width modulator, to produce a square wave, or a high-speed, for example, 0 Hz to 1 GHz, Direct Digital Synthesis (DDS) component. This second waveform at frequency ($f_2$) is used to mix (multiply) both the output waveform of the system 330 and the input waveform to the system 330. The system 330 may be any of the systems detailed above for the system 30 of FIG. 1. A luminescent system is typical as the system 330.

The result of this process is that a sum frequency, $f_1+f_2$, and difference frequency, $f_1-f_2$, are generated at the output of mixers 338a and 338b. The second frequency ($f_2$) is chosen so that the difference between the first excitation frequency ($f_1$) and the second mixer frequency ($f_2$), $f_1-f_2$ is less than the Nyquist frequency of the ADCs. This requirement allows the ADC 340a, 340b to sample the waveforms without aliasing. The sum frequency is usually much greater than the Nyquist frequency so it is easy to filter out using a low pass filter (LPF) 339a, 339b, for each of the channels. This apparatus 310 is particularly useful, in that the down-converted difference frequency from mixer 338a still retains the phase and amplitude information of the original higher frequency output waveform as explained below. Thus the phase shift, $\Delta\theta$, and amplitude $A_S$ through the System 330, detector 334 and amplifier 336 at an excitation modulation frequency of $f_1$, can be preserved and transferred to the lower frequency $f_1-f_2$.

For sinusoidal waveforms, the mixing process in the mixer 338b can be written as follows:

$$x_1(t) = A_S A_1 \sin(2\pi f_1 t + \phi_1 + \Delta\theta) \qquad \text{Eq. 10}$$

$$x_2(t) = A_1 \sin(2\pi f_1 t + \phi_1) \qquad \text{Eq. 11}$$

$$m(t) = A_2 \sin(2\pi f_2 t + \phi_2) \qquad \text{Eq. 12}$$

$$y_1(t) = x_1(t) * m(t) \qquad \text{Eq. 13}$$

$$y_2(t) = x_2(t) * m(t) \qquad \text{Eq. 14}$$

and, $$y_1(t) = A_S \frac{A_1 A_2}{2} \cos(2\pi(f_1 - f_2) + \phi_2 - \phi_1 - \Delta\theta) + \qquad \text{Eq. 15}$$
$$A_S \frac{A_1 A_2}{2} \cos(2\pi(f_1 + f_2) + \phi_2 + \phi_1 + \Delta\theta)$$

$$y_2(t) = \frac{A_1 A_2}{2} \cos(2\pi(f_1 - f_2) + \phi_2 - \phi_1) + \qquad \text{Eq. 16}$$
$$\frac{A_1 A_2}{2} \cos(2\pi(f_1 + f_2) + \phi_2 + \phi_1)$$

where, $f_1$, $\phi_1$, $A_1$ are excitation waveform frequency, phase and amplitude respectively;

$f_2$, $\phi_2$, $A_2$ are mixing waveform frequency, phase and amplitude respectively;

$A_S$, is the amplitude of the system;

$\Delta\theta$, is the phase shift caused by the system;

$x_1(t)$, is the input to the mixer 338a, comprising output of system 330, having phase $\Delta\theta+\phi_1$ and amplitude $A_1 A_S$;

$x_2(t)$, is the input to the mixer 338b, comprising the excitation waveform, having phase $\phi_1$ and amplitude $A_1$;

$m(t)$, is the mixing waveform input to the mixers 338a and 338b;

$y_1(t)$, is the output waveform of the mixer 338a; and, $y_2(t)$, is the output waveform of the mixer 338b.

The multiplication of the two sine waves of different frequencies generate two other sine waves, one of which is at the difference frequency and the other at the sum frequency, as shown by Eqs. 10, 12, 13 and 15 for the mixer 338a, and Eqs. 11, 12, 14 and 16 for the mixer 338b. The other significant result is that the phase information of both the excitation waveform and the mixing waveform is retained in the mixing process. According to the equations above for the mixer 338a, the output of the mixer 338a is a waveform at sum, $f_1+f_2$, and difference, $f_1-f_2$, frequencies. The output of the mixer 338a is filtered by LPF 339a, resulting in a waveform with a difference in frequencies $f_1-f_2$, and according to Equation 15 above, there is a phase $\theta_a=\Delta\theta+(\phi_1-\phi_2)$, and an amplitude $A_a=A_1 A_2 A_S/2$.

Correspondingly the result of mixing in 338b is similarly explained. According to the equations 11, 12, 14 and 16 above for mixer 338b, the output of 338b is a waveform with sum, $f_1+f_2$, and difference, $f_1-f_2$, frequencies. The output of mixer 338b is filtered by LPF 339b, resulting in a waveform with a difference in frequencies $f_1-f_2$, and according to Equation 16 above, there is a phase $\theta_b=(\phi_1-\phi_2)$, and an amplitude $A_b=A_1 A_2/2$.

Since the mixing waveform is used in both mixers 338a, 338b to mix the output of the system 330 as well as the input to the system 330, the phase $\phi_2$ of the mixing waveform can be removed by computing a phase difference, $\theta_a - \theta_b$, in the digital processor 320.

The phase shift of the system 330, detector 334 and amplifier 336, represented as $\Delta\theta$, is computed by making two phase measurements, one from the output of ADC 340a, known as the total phase and expressed as $\theta_{total} = \Delta\theta + (\phi_1 - \phi_2)$, shown as $\theta_a$ output from LFC 345a, and a phase measurement from the other ADC 340b, known as the reference phase, expressed as $\theta_{ref} = (\phi_1 - \phi_2)$, shown as $\theta_b$ output from LFC 345b. The IIR filters, in accordance with the IIR filter 46a of FIG. 2B, detailed above, are executed in parallel, as the output from each ADC 340a, 340b is inputted to corresponding linear filter components 345a, 345b in the digital processor 320. In each of the linear filter components 345a, 345b, after N samples are received over k excitation cycles and linearly filtered according to Equation 3 (Eq. 3), the real component R(w) and the imaginary component I(w) of the transfer function H(jw) of Equation 2 (Eq. 2) are calculated as Equation 4 and Equation 5, as detailed above, to determine the requisite phases ($\theta_{total}$ and $\theta_{ref}$), each phase, $\theta_{total}$ and $\theta_{ref}$, calculated with the "6" series equations.

The equation to determine the phase shift $\Delta\theta$ of the system 330, detector 334, and amplifier 336 is expressed as, Equation 9.2, as:

$$\Delta\theta = \theta_{total} - \theta_{ref} \qquad \text{Eq. 9.2}$$

as explained above the ($\phi_1 - \phi_2$) components for each waveform pair cancel each other.

As long as the IIR filters can execute in the time between samples from the ADC 140, each of these will contain all the phase shifts contributed by the analog, digital components, and the luminescent sample of the system 330. The difference in the phase shifts will be only the phase shift due to system 330, detector 334 and amplifier 336, but uncontaminated by other system delays, either analog or digital The phase shift ($\Delta\theta = \theta_{total} - \theta_{ref}$), as detailed above, provides a value used to characterize the luminescent system's response, and is used, for example, to calculate a luminescent lifetime, or related to analyte concentration.

The amplitude ratio of the system 330, represented as $A_S$, is computed by making two amplitude ratio measurements, one from the output of ADC 340a, known as the total amplitude, and expressed as $A_{total}$, and an amplitude from the other ADC 340b, known as the reference amplitude, expressed as $A_{ref}$. Both amplitude ratios are modeled by Equations 15 and 16, as detailed above. The IIR filters, in accordance with the IIR filter 46a of FIG. 2B, detailed above, are executed in parallel, as the output from each ADC 340a, 340b is inputted to corresponding linear filter components (LFC) 345a, 345b in the digital processor 320. In each of the linear filter components 345a, 345b, after N samples are received over k excitation cycles and linearly filtered according to Equation 3 (Eq. 3), the real component R(w) and the imaginary component I(w) of the transfer function H(jw) of Equation 2 (Eq. 2) are calculated as Equation 4 and Equation 5, as detailed above, with the requisite amplitudes obtained ($A_{total}$ and $A_{ref}$) calculated with Equation 7. For both pairs of waveforms, a ratio according to Equation 8.2, as detailed above, is now applied, and for both pairs of waveforms, $A_1A_2/2$ in each waveform pair, is an unknown value, not equal to zero or 1. Accordingly, Equation 8.2 for each waveform pair, is expressed as:

$$A_{total} = A_1 A_2 A_S / 2 \qquad \text{Eq. 8.2.1}$$

$$A_{ref} = A_1 A_2 / 2 \qquad \text{Eq. 8.2.2}$$

The equation to determine Amplitude for the system 330 ($A_S$) is expressed as, Equation 17, as:

$$A_S = A_{total} / A_{ref} \qquad \text{Eq. 17}$$

as the $A_1$ and $A_2$ components for each waveform pair cancel each other.

FIG. 9 shows an apparatus 410, that uses a digital processor 420, with linear filter components (LFC) 445a, 445b. The digital processor 420 includes a microcontroller. The apparatus 410 operates in a down-converting mode (by virtue of using a mixer 438). The down-converting mode extends the range of excitation modulation frequencies to measure shorter luminescent lifetimes. Without the down-conversion, the highest modulation frequency for this system 430 would be about 16 KHz because the sample rate is 31.25 KHz. With down-converting the highest modulation frequency could be as high as 250 KHz.

For example, the apparatus 410 of FIG. 9 may use an excitation modulation frequency, $f_1$, of about 123 KHz. The requisite parameters are as follows:
Crystal Oscillator Frequency (CLK): 8 MHz
ADC Sample Rate (Fs): 31.250 kHz
Crystal to ADC ratio (R): 256
PWM Mixer Frequency ($f_2$): 8 MHz/64=125.0000 kHz
PWM Excitation Frequency ($f_1$): 8 MHz/65=123.0769 kHz
Crystal to Mod. Frequency Ratio (M): M=65
Difference Frequency $f_2-f_1$ ($f_{diff}$): $f_2-f_1$=1923.076923 Hz
Sum Frequency $f_2+f_1$ ($f_{sum}$): $f_2+f_1$=248076.9230 Hz
Total Samples (N): N=M*17=1105
Frequency Index (k):

$$k = \left(\frac{R - 4M}{M}\right) N = 68$$

Second Order filter coefficient:

$$C_2 = 2\cos\left(\frac{2\pi k}{N}\right) = 2\cos\left(\frac{2\pi 68}{1105}\right) = 1.852349 \qquad \text{Eq. 18.1}$$

Second Order filter:

$$v_{68}(n) = C_2 v_{68}(n-1) - v_{68}(n-2) + x(n) \qquad \text{Eq. 18.2}$$

By choosing the window length (N) to be a whole number multiple of the crystal to modulation frequency ratio (M) this gives a whole number value for the frequency index k. Equation 18.1 shows the Second Order filter coefficient for the given values for k and N. The sum frequency is shown above to illustrate that this frequency is well outside of the bandwidth of the ADCs 440a, 440b and is easily attenuated by each low-pass filter (LPF) 439a, 439b, before it is sampled by the ADC 440a, 440b.

The apparatus 410 includes a microcontroller with two ADCs 440a, 440b, typically internal thereto, that send their respective output, $x_1(n)$ and $x_2(n)$, (signals) to the respective linear filter components 445a, 445b, that are implemented by the microcontroller (of the digital processor 420).

The apparatus 410 also includes two pulse width modulators (PWM) 423a (PWM1) and 423b (PWM2), that generate a square wave excitation signal at frequency $f_1$ and a square wave mixing signal at frequency $f_2$. The two pulse width modulators (PWM1, PWM2) 423a, 423b may also be direct digital synthesis (DDS) engines that generate sign wave functions, and the apparatus 410 would operate similar to the operation detailed below.

The square wave output of PWM1 423a drives a source 428, comprising a driver 428a that modulates an excitation (EXC.) LED 428b at frequency $f_1$. The square wave output of PWM1 423a also connects to differential amplifier 438b. The excitation LED 428b directs excitation light to the system 430, for example, a luminescent sample or probe 430a, typically through an excitation filter 429.

The square wave output of PWM2 423b connects to the switch component 438c or multiplexing switch of mixer 438, and causes the switch component 438c to actuate at frequency $f_2$. There is an analog mixer 438, formed of differential amplifiers (D. Amp) 438a, 438b coupled to the switch component 438c, that includes a single-pole-double-throw (SPDT) switch, formed of two switches 438c' and 438c''. Each switch 438c' and 438c'' is coupled with a corresponding differential amplifier 438a, 438b. The outputs of the differential amplifiers 438a, 438b are fed into the input of the switch component 438c.

The emission of luminescent sample or probe 430a, typically passes through an emission filter 431, and is converted to an electrical signal by the detector 434, for example, including a photodiode (e.g., a PIN photodiode) and a transducer (as detailed above for detectors 34, 134, 234 and 334), with the signal amplified by amplifier 436, and then sent to the differential amplifier 438a. The output of 438a is also fed into the inputs of the switch component 438c, in particular switch 438c'. The switch 438c' position is controlled by a periodic square wave at the mixing frequency, $f_2$, that is supplied by PWM2 423b. This combination effectively multiplies the signal by plus and minus one. The apparatus 410, by using SPDT switches, may have up to as many as four SPDT switches in a single package. This allows for four mixers in one small package.

This combined mixing approach has some advantages. One advantage is that the mixing frequency has a wide dynamic range with some components going up to 100 MHz and extending all the way down to DC, for example, less than 10 Hz. The mixers 338a, 338b can be turned off completely, by setting the output of 324b to one state when down-conversion is not required, such as when the source modulation frequency, $f_1$, is less than the Nyquist frequency of the ADCs 340a, 340b. A second advantage is that this is a linear operation that will not cause distortion due to the mixing process.

In this down-converting apparatus 410, two linear filter components 445a, 445b are executed contemporaneously, and typically simultaneously (in parallel), within the sample period of the ADCs 440a, 440b, to obtain two phase shifts of the data stream from each channel, expressed as $\Delta\theta_a$ (whose input is the output from ADC 440a) and $\Delta\theta_b$ (whose input is the output from ADC 440b), respectively. From these two phase shifts $\Delta\theta_a$ and $\Delta\theta_b$ the phase shift of the system 430, expressed as $\Delta\theta$, is computed and obtained. The ADC 440a is from the system, and defines a system or "total" channel, while the ADC 440b is from a reference, and defines a "reference" channel.

The second order IIR filters (in accordance with the IIR filter 46a shown in FIG. 2B and described above) of linear filter components 445a and 445b operate in parallel as data streams $x_1(n)$ and $x_2(n)$ are received. Both phase shifts ($\Delta\theta_a$ and $\Delta\theta_b$) are modeled by Equations 1 and 2, as detailed above. The IIR filters typically execute in parallel, as the output from each ADC 440a, 440b is inputted to corresponding linear filter components 445a, 445b in the digital processor 420. In each of the linear filter components 445a, 445b, after N samples are received over k excitation cycles and linearly filtered according to Equation 3 (Eq. 3), the real component R(w) and the imaginary component I(w) of the transfer function H(jw) of Equation 2 (Eq. 2) are calculated as Equation 4 and Equation 5, as detailed above, to determine the requisite phases ($\theta_a$ and $\theta_b$) each phase, $\theta_a$ and $\theta_b$, calculated with the "6" series equations.

Both pairs of waveforms output from the mixer 438, and processed by the linear filter components 445a, 445b, have phase and amplitude as predicted by Equations 6.1-6.6 and 7, detailed above. That is, for each waveform pair, Equation 8.1 is expressed as:

$$\theta_{a(total)} = \Delta\theta + (\phi_1 - \phi_2) \qquad \text{Eq. 8.1.1'}$$

$$\theta_{b(ref)} = (\phi_1 - \phi_2) \qquad \text{Eq. 8.1.2'}$$

The computed reference phase for ADC reference channel (from ADC 440b) is subtracted from the computed signal phase for ADC system or total channel (from ADC 440a), in accordance with, Equation 9.2, as:

$$\Delta\theta = \theta_{a(total)} - \theta_{b(ref)} \qquad \text{Eq. 9.2.1}$$

whereby the phase difference represents the phase shift through the system 430, detector 434, and amplifier 436.

The quantity $\Delta\theta$, from Equation 9.2.1, may then be used to calculate an analyte concentration using a theoretical or empirically derived calibration model, or the time constant (lifetime) of the system 430 can be calculated When the time constant or lifetime of the luminescent sample or probe 430a is relatively long, the mixer 438 can be turned off by setting the PWM2 423b output in a fixed state either high or low. In this case a mixing function is not performed and the highest modulation is limited to approximately 16 kHz.

While preferred embodiments of the disclosed subject matter have been described, so as to enable one of skill in the art to practice the disclosed subject matter, the preceding description is intended to be exemplary only. It should not be used to limit the scope of the disclosure, which should be determined by reference to the following claims.

What is claimed is:

1. A method for analyzing light emissions from a luminescent sample comprising the following steps:
   a. providing excitation light to a luminescent sample;
   b. detecting emitted luminescence from the luminescent sample;
   c. sampling the detected luminescence to create a digital signal;
   d. analyzing the emitted luminescence by processing the digital signal with a linear second-order digital IIR filter applying at least a portion of a modified Goertzel algorithm; and
   e. transforming the linearly-filtered digital signal using control logic to compute a real portion and an imaginary portion to determine the phase shift between the excitation light and the emitted luminescence.

2. The method of claim 1, wherein the real and imaginary portions are used for determining the amplitude of the emitted luminescence.

3. The method of claim 1, wherein the excitation step is performed by at least one light emitting diode.

4. The method of claim 1, wherein the detecting step is performed by at least one photodiode.

5. The method of claim 1, wherein the excitation light varies sinusoidally or as a square wave.

6. A luminescent light measurement apparatus comprising:
   a. an excitation light source configured to transfer excitation light to a fluid medium;
   b. a luminescent probe configured to transfer emission light in response to the excitation light;

c. a detector system configured to detect the emission light and generate an analog signal corresponding to the emission light;

d. a converter for converting the analog signal into a digital signal; and e. a digitally-implemented linear second-order IIR filter for applying at least a portion of a modified Goertzel algorithm to the digital signal; and f. a processor programmed to transform the linearly filtered digital signal using control logic to compute a real portion and an imaginary portion and to determine a phase shift between the excitation light and the emission light.

7. The apparatus of claim 6, wherein the excitation light source includes at least one light emitting diode.

8. The apparatus of claim 6, wherein the detector system includes at least one photodiode to detect the emission light.

9. The apparatus of claim 6 including a processor programmed to implement the linear filter component to determine a phase shift between the excitation light and the digital signal corresponding to the emission light.

10. The apparatus of claim 6 including a processor programmed to implement the linear filter component to determine the amplitude of the digital signal corresponding to the emission light.

11. The apparatus of claim 6, where the excitation light source is modulated sinusoidally or as a square wave.

12. A method for analyzing light emissions from a luminescent sample comprising the following steps:

a. providing excitation light to a luminescent sample;

b. detecting emitted luminescence from the luminescent sample;

c. sampling the detected emitted luminescence to create a first digital signal;

d. processing the first digital signal with a linear second-order digital IIR filter applying at least a portion of a modified Goertzel algorithm to create a first filtered signal;

e. transforming the first filtered signal using control logic to compute a real portion and imaginary portion to determine a first phase shift between the excitation light and the first digital signal;

f. providing reference light to the luminescent sample;

g. detecting emanated reference light from the luminescent sample;

h. sampling the detected emanated reference light to create a second digital signal;

i. processing the second digital signal with the linear second-order digital IIR filter applying at least a portion of the modified Goertzel algorithm to create a second filtered signal;

j. transforming the second filtered signal using control logic to compute a real portion and imaginary portion to determine a second phase shift between the reference light and the second digital signal; and k. subtracting the first phase shift from the second phase shift to determine the phase difference between the excitation light and the emitted luminescence.

13. An apparatus for analyzing light emissions from a luminescent sample, comprising:

a. a luminescent sample comprising first and second surfaces that emanates luminescent light in response to excitation light and reference light in response to reference light;

b. an excitation light source opposed to the first surface so that luminescent light emanates from the luminescent sample;

c. a reference light source opposed to one surface so that reference light emanates from the luminescent sample;

d. a detector of luminescent and reference light opposed to one surface so that luminescent light and reference light are detected;

e. an analog-to-digital converter connected to the output of the detector;

f. a filter connected to the analog-to-digital converter, the filter being a linear second-order digital IIR filter applying at least a portion of a modified Goertzel algorithm;

g. control logic connected to the filter that computes
   (1) real and imaginary portions of the filter output corresponding to the luminescent light and then a first phase shift based on those portions;
   (2) real and imaginary portions of the filter output corresponding to the reference light and then a second phase shift based on those portions;

h. a subtractor connected to the control logic that subtracts the first phase shift from the second phase shift to determine the phase difference between the excitation light and the luminescence light.

14. The system of claim 13 in which the luminescent light source and the reference light source are illuminated sequentially so that only one source is on at a time.

15. The system of claim 13 in which the reference light source is opposed to the first surface of the luminescent sample.

16. The system of claim 13 in which the detector is opposed to the first surface of the luminescent sample.

* * * * *